US006620474B1

(12) United States Patent
Regnier et al.

(10) Patent No.: US 6,620,474 B1
(45) Date of Patent: Sep. 16, 2003

(54) MULTILAYER FILMS WITH QUIET FILM LAYER HAVING NOISE DAMPENING PROPERTIES

(75) Inventors: Francois J. F. Regnier, Weyersheim (FR); Harvey C. Tung, Newark, OH (US); Rochelle A. Woods, Midland, MI (US); Jeffrey E. Bonekamp, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/251,356

(22) Filed: Sep. 20, 2002

Related U.S. Application Data

(62) Division of application No. 09/605,496, filed on Jun. 28, 2000, now Pat. No. 6,455,161.
(60) Provisional application No. 60/141,744, filed on Jun. 30, 1999, now abandoned.

(51) Int. Cl.$^7$ .................. B32B 27/08; B32B 27/30; B32B 27/32; B32B 27/34; B32B 27/36
(52) U.S. Cl. .................. 428/35.7; 428/35.2; 428/413; 428/423.1; 428/424.8; 428/474.4; 428/476.3; 428/476.9; 428/480; 428/483; 428/500; 428/515; 428/516; 428/517; 428/518; 428/519; 428/520; 428/521; 428/522; 428/523; 604/332
(58) Field of Search .................. 428/34.1, 35.2, 428/35.4, 35.7, 36.6, 36.7, 36.9, 412, 480, 483, 413, 474.7, 475.5, 500, 515, 516, 517, 518, 520, 521, 522, 523, 519, 212, 424.2, 423.1, 424.8, 474.4, 476.3, 476.8; 604/332, 338, 339

(56) References Cited

U.S. PATENT DOCUMENTS

| 4,376,799 A | * | 3/1983 | Tusim ..................... 428/213 |
| 5,308,894 A | | 5/1994 | Laughner ................. 523/436 |
| 5,369,154 A | | 11/1994 | Laughner ................. 523/436 |
| 5,461,092 A | | 10/1995 | Laughner ................. 523/436 |
| 5,468,807 A | | 11/1995 | Tsurutani ................. 525/240 |
| 5,496,295 A | | 3/1996 | Wilfong et al. .......... 604/332 |
| 5,567,489 A | | 10/1996 | Allen et al. |
| 5,616,420 A | | 4/1997 | Yamaoka ................. 428/515 |
| 5,643,375 A | | 7/1997 | Wilfong et al. ....... 156/244.24 |
| 5,658,625 A | | 8/1997 | Bradfute et al. .......... 428/34.9 |
| 5,703,187 A | | 12/1997 | Timmers ................. 526/282 |
| 5,730,919 A | * | 3/1998 | Wilfong et al. ....... 264/173.11 |
| 5,872,201 A | | 2/1999 | Cheung et al. ........... 526/282 |
| 5,948,839 A | * | 9/1999 | Chatterjee ............... 524/108 |
| 5,983,604 A | * | 11/1999 | Wilfong et al. ............ 53/449 |
| 6,143,383 A | * | 11/2000 | Giori ..................... 428/35.2 |
| 6,258,423 B1 | * | 7/2001 | Giori ..................... 428/36.7 |
| 6,455,161 B1 | * | 9/2002 | Regnier et al. ........... 428/412 |

FOREIGN PATENT DOCUMENTS

| EP | 056 323 A1 | 7/1982 |
| EP | 418 836 A3 | 3/1991 |
| EP | 588 667 A2 | 3/1994 |
| EP | 641 647 | 3/1995 |
| EP | 700 777 A1 | 3/1996 |
| EP | 0 780 214 A1 | * 6/1997 |
| EP | 527 589 | 6/1998 |
| WO | WO 95/07816 | 3/1995 |
| WO | WO 95/07817 | 3/1995 |
| WO | WO 98/10014 | 3/1998 |

OTHER PUBLICATIONS

"The Viscoelastic Properties of Rubber–Resin Blends", Parts I, II, and III, *Journal of Applied Polymer Science*, Vo.l. 30, J. B. Class et al, pp. 805–842, (1985).
"Light and Stable Resins for Hot–melt Adhesives", P. Dunckley, *Adhesives Age*, Nov. 1993.
"A Statistical Approach to Formulating Deep Freeze HMAs", W. J. Honiball et al, *Adhesive Age*, pp. 18–26, May 1997.
"Tackifier Resins", J. A. Schlademan, *Handbook of Pressure Sensitive Adhesive Technology*, Ch. 20, pp. 527–544.
"Polyester", Ch. 19G, *Film Extrusion Manual*, p. 533, TAPPI Press, (1992).
*Woods Practical Guide to Noise Control*, 5$^{th}$ Edition, p. 117, Woods Acoustics, Mar., (1972).
"Polymer Permeability", J. Comyn, pp. 11–74, Elsevier Applied Science Publishers, (1985).
"Polymer Science Dictionary", Elsevier Applied Science Publishers, (1989).
"The Use of Barrier Polymers in Food and Beverage Packaging",*Plastic Film Technology, High Barrier Plastic Films for Packaging*, vol. 1, M. Salame, pp. 132–145 (1989).
"Identification of Specific Trace Levels of Chemicals in Human Feces", Dmitriev M.T., *Lab Delo*, (1985), vol. 10, 608–14 (Non–English).
"Gas–Chromatographic and Mass–Spectrometric Analysis of the Odour of Human Feces", J.G. Moore, *Gastroenterology*, vol. 93, pp. 1321–1329, (1987).
"Only the Nose Knows", *Gastroenterology*, vol. 93, No. 6, pp. 1437–1438, (1987).
"Influence of Nutritional Substrates on the Formation of Volatiles by the Fecal Flora" M. Hiele, *Gastroenterology*, vol. 100, pp. 1597–1602, (1991).

(List continued on next page.)

Primary Examiner—Vivian Chen

(57) ABSTRACT

Multilayer films comprising a quiet film layer having noise dampening properties and at least one second layer which are particularly useful for, ostomy bags (colostomy, ileostomy), trans-dermal delivery systems (TDDS), cosmetic patches, incontinence bags, medical collection bags, parenteral solution bags, and food packaging, as well as for protective clothing and soil fumigation applications. The quiet layer comprises a polymer resin or polymer resin composition having a Tangent Delta value of at least 0.25 at a temperature within the range of $-5°$ C. and $15°$ C. or at least 0.32 at a temperature within the range of $-12°$ C. to $-5°$ C., and the at least one second layer has a storage modulus G' equal to or greater than $2\times10^4$ N/cm$^2$.

7 Claims, No Drawings

OTHER PUBLICATIONS

"Screening Method for the Determination of Volatiles in Biomedical Samples", Y. Ghoos, *Journal of Chromatography*, vol. 665, pp. 333–345 (1994).

"Influence of Dietary Protein Supplements of the Formation of Bacterial Metabolites in the Colon", B. Geypens, *GUT*, (1997), vol. 41, pp. 70–76.

"A New General Purpose Quantum Mechanical Molecular" *J. Am. Chem. Soc.*, M. J. S. Dewar et al., vol. 107, pp. 3902, (1985).

"Carbon–13 NMR Method", *Polymer Sequence Determination*, J. C. Randall, pp. 71–78, Academic Press New York, (1977).

\* cited by examiner

MULTILAYER FILMS WITH QUIET FILM LAYER HAVING NOISE DAMPENING PROPERTIES

CROSS REFERENCE STATEMENT

This application is a Divisional of U.S. application Ser. No. 09/605,496, filed Jun. 28, 2000, U.S. Pat. No. 6,455,161, which claims the benefit of U.S. Provisional Application No. 60/141,744, filed Jun. 30, 1999, now abandoned.

This invention relates to essentially amorphous, non-chlorinated polymeric films and to the use of such films as effective barriers to odors and organic molecules.

Multilayer structures, which are substantially impervious to gases and/or moisture, are well known in the medical and food packaging industries. Currently, poly(vinylidene chloride) (PVDC) is used as one of the materials of choice for the gas barrier component of barrier films. For ostomy applications (i.e., colostomy and ileostomy), a film of PVDC sandwiched between opposing layers of low density polyethylene (LDPE) is widely used, with PVDC functioning as the gas barrier, and LDPE as the structural and sealant layer. Also, polyvinyl chloride (PVC) or chlorinated polyethylene (CPE) blended with ethylene-vinyl acetate copolymer (EVA) can be used in the structural and sealant layer, or other layers, of such a structure.

However, disposal of these chlorine-containing materials presents a number of potential environmental concerns, especially relating to incineration of these materials after use in hospitals or otherwise. In addition, exposure to di-2-ethylhexyl-phthalate (DEHP), a common plasticizer utilized with PVDC and PVC, may present a number of health-related concerns, including reduced blood platelet efficacy, and potential links to liver cancer.

Non-chlorine containing polymeric resins, such as ethylene-vinyl alcohol copolymers (EVOH), are also used as barrier layers and have been suggested for ostomy applications. However, while the barrier properties of EVOH copolymers are very high under dry conditions, they rapidly deteriorate in the presence of moisture. Thus, EVOH copolymers are not desirable for ostomy applications.

U.S. Pat. No. 5,496,295, U.S. Pat. No. 5,658,625 and U.S. Pat. No. 5,643,375 describe multilayer barrier films and articles made thereof. These films are useful, among others, in ostomy applications, and comprise a gas barrier layer of a chlorine-free organic polymer, which is substantially impermeable to oxygen gas, and a moisture barrier layer of a mesophase propylene-based material. The chlorine-free organic polymer gas barrier layer includes vinyl alcohol polymers, such as EVOH copolymers, polyvinyl alcohol (PVOH), polyacrylonitrile, polystyrene, polyester and nylon either alone or blended with each other. The moisture barrier layer comprises a mesophase propylene polymer-based material, such as mesomorphous polypropylene, mesopolymer blends and/or mesocopolymers. Quenching a propylene-based material from the melt state forms the mesophase propylene-based material.

EP 0 700 777 A1 describes a chlorine-free multilayer film useful for manufacturing bags or pouches for ostomy/urostomy applications and comprising a seven layer structure. This structure comprises a gas barrier layer of a chlorine-free organic polymer which is substantially impermeable to oxygen, such as one of the above vinyl alcohol polymers, polyamides, polyesters and polystyrenes; two tie layers each contacting one side of said barrier layer; an inner surface layer; an outer surface layer and two intermediate layers positioned between said surface layers and comprising an ethylene-propylene (EP) copolymer.

EP 0 418 836 A3 describes multilayer oriented films suitable for use in the food packaging industry and having layers of a propylene homopolymer or copolymer, a co-polyester layer and an adhesive layer of a polar-modified polyolefin located between, and bonded to, the propylene polymer and co-polyester layers.

EP 0 056 323 A1 describes a thermoformable laminate for a sterilizable packaging comprising a cast layer of polyester, including polybutylene terephthalate, glycol-modified polyethylene terephthalate (PET-G), and a copolymer of cyclohexane dimethanol and terephthalic acid, joined by a bonding layer consisting of polypropylene (PP), LDPE or an ionomer resin. However, since such structures are targeted for thermoformable packaging applications, they possess high modulus and, therefore, cannot provide the required level of quietness needed for ostomy bag application as a result of the relatively rigid polymers used for skins composition. Additionally, the Tangent Delta (Tan Δ) value of the skin polymers (LDPE, crystalline PP and ionomer resins) of these laminates indicate that they do not provide a quiet film as described below.

EP 0 588 667 A2 describes a multilayer film useful in moisture barrier packaging applications having at least one layer comprising a blend of propylene polymer or copolymer and a hydrocarbon resin and two additional layers comprising a propylene homopolymer or copolymer, an ethylene-alpha-olefin (EAO) copolymer, an ionomer, polybutylene or blends thereof. A core layer of an EVOH copolymer or another oxygen barrier material or high density polyethylene (HDPE) can be included in some embodiments.

Attempts to find additional chlorine-free polymeric films suitable for use as barrier layers have been guided by a generally held belief that a polymer having good oxygen barrier properties would also exhibit good barrier properties to organic products and odors. (See, for example, "Plastic Film Technology, High Barrier Plastic Films for Packaging", volume 1: The use of Barrier Polymers in Food and Beverage Packaging, M. Salame, pp. 132–145 (1989)). Therefore, attempts to find polymeric films with sufficient barrier properties for use in the medical and food-packaging industries have focused upon the oxygen permeability of a given polymeric film. However, the inventors of the present application have found that not all polymers having low oxygen permeability exhibit odor barrier properties sufficient for ostomy applications and vice versa.

Studies have shown that human feces contain more than 122 volatile compounds as analyzed by gas chromatography/mass spectrometry. (See "Identification of Specific Trace Levels of Chemicals in Human Feces", Dmitriev M. T., *Lab. Delo* (1985), (10), 608–14; "Gas-Chromatographic and Mass-Spectrometric Analysis of the Odour of Human Feces", J. G. Moore, *Gastroenterology*, 1987, 93, 1321–9; M. D. Levitt, "Only the Nose Knows", *Gastroenterology*, 1987, vol. 93, No. 6, 1437–8; "Influence of Nutritional Substrates on the Formation of Volatiles by the Fecal Flora", M. Hiele, *Gastroenterology*, 1991, 100, 1597–1602; "Screening Method for the Determination of Volatiles in Biomedical Samples"; Y. Ghoos, *Journal of Chromatography*, 665, 1994, 333–345; and "Influence of Dietary Protein Supplements on the Formation of Bacterial Metabolites in the Colon", B. Geypens, *GUT*, 1997, 41, 70–76.)

These studies indicate that compounds responsible for fecal odor are mainly indoles and sulfide derivatives. Thus, compounds having relatively small molecules, such as, for example, hydrogen sulfide ($H_2S$) or methyl mercaptan ($CH_3SH$), compounds having larger molecules, such as, for example, ethyl sulfide, dimethyl disulfide (DMDS) or diethyl disulfide (DEDS), and compounds having large molecules, such as, for example, dimethyl trisulfide, indole or 3-methyl indole, are responsible for fecal odor.

Therefore, there remain needs in the art for polymeric films which (a) are environmentally safe, (b) are hydrolytically stable, and (c) exhibit low permeability to both small and larger molecular diameter odor-causing molecules. Furthermore, depending upon the end-use of such films, there remains the need for these films to be quiet, i.e., having low noise emission when crumpled.

Those needs are met by the present invention. Thus, the present invention provides essentially amorphous, non-chlorinated (or chlorine-free) polymer films useful as barriers to odors and organic compounds, as well as methods of using such films as barriers to odors and organic molecules in a monolayer or a multilayer film structure.

A first embodiment of the present invention is an essentially amorphous, non-chlorinated polymer film, the film functioning as a barrier to at least one of odors and organic molecules that have a diameter of 0.40 nanometer (nm) or more ($\geq$) with barrier functionality being determined by at least one of a) a 3-methyl indole breakthrough time of at least($\geq$) five hours, b) a DEDS breakthrough time of at least 40 minutes (min) or c) a $H_2S$ permeation rate less than or equal to ($\leq$) 60 cubic centimeters ($cm^3$) of $H_2S$ per square centimeter ($cm^2$) of film area per day ($cm^3/cm^2$-day), as well as a method of using such films as barriers to odors and organic molecules in either a monolayer or a multilayer film structure.

A second embodiment provides multilayer film structures containing $\geq$ one layer of the film of the first aspect and $\geq$ one quiet film layer that has reduced noise emission, said quiet film layer comprising $\leq$ one polymeric resin or polymeric resin composition having a Tan $\Delta$ value $\geq$ 0.25 at a temperature within the range between $-5°$ centigrade (° C.) and $15°$ C., or $\geq$ 0.32 at a temperature within the range of from $-12°$ C. to $-5°$ C. The multilayer film structures desirably function as barriers to molecules having a diameter $\geq$ 0.40 nm.

A third embodiment provides a method of reducing the emission of noise in a multilayer film structure containing $\geq$ one layer of the film of the first embodiment, the method comprising the steps of: a) blending a first polymer resin, polymer resin composition or polymer blend composition having a Tan $\Delta$ value $\geq$ 0.25 at a temperature within the range between $-5°$ C. and $15°$ C. or $\geq$ 0.32 at a temperature within the range of from $-12°$ C. to $-5°$ C. with a second polymer resin; and b) forming a polymer film layer of the multilayer film from the blended polymer resins, wherein the first polymer resin or polymer resin composition comprises $\geq$ 25 percent by weight (wt %), based on total layer weight.

The polymeric barrier films of the present invention are particularly useful for ostomy bags (colostomy, ileostomy), trans-dermal delivery systems (TDDS), cosmetic patches, incontinence bags, medical collection bags, parenteral solution bags, and packaging of odorous food or products, as well as for protective clothing applications or soil fumigation.

As stated above, the present invention provides essentially amorphous, non-chlorinated polymer films, which are useful as barriers to odors and organic compounds, as well as methods of using such films, in a monolayer or multilayer film structure, as barriers to odors and organic molecules.

As used herein, "essentially amorphous" means containing less than (<) 8 wt % non-amorphous polymer(s), based on total polymer weight. Moreover, it refers to amorphous polymers that have not been prepared through quenching. "Quenching", as used herein, means rapid cooling of the polymer from its melt state down to a sub-ambient temperature (below approximately 20° C.). "Non-chlorinated" means that a polymer contains substantially no chlorine (i.e., <1 wt %, based on total polymer weight).

The terms "relatively small", "larger" and "large" molecules, as used herein, refer to relative sizes as determined by respective critical molecular diameter (CMD). "Relatively small" molecules include molecules having a CMD of 0.40 nm up to 0.55 nm. "Larger" molecules include molecules having a CMD of more than (>) 0.55 nm and up to 0.70 nm, and "large" molecules include molecules having a CMD >0.70 nm.

The calculated CMD of oxygen is 0.33 nm, 0.40 nm for $H_2S$, 0.50 nm for methyl sulfide, 0.55 nm for DMDS, 0.57 nm for ethyl sulfide, 0.58 nm for DEDS, 0.63 nm for dimethyl trisulfide, 0.74 nm for indole and 0.78 nm for 3-methyl indole. CMD determination uses a SPARTAN 5.1.1. program (molecular orbital program marketed by WAVEFUNCTION Inc., California 92612, USA).

Molecular structures are optimized by energy minimization using semi-empirical quantum mechanics models (AM1 method: M. J. S. Dewar, E. G. Zoebisch, E. F. Healy, and J. J. P. Stewart, J. Am. Chem. Soc. 107, 3902 (1985). AM1: A New General Purpose Quantum Mechanical Molecular) contained in the Spartan program version 5.1.1. Conformational analysis is carried out in order to obtain structures in their minimum-energy conformations. The CMD is obtained from the space-filling (CPK) representation of the optimized structure. The box size is adjusted in order to contact the van der Waals spheres. The molecular diameter is taken as the second-largest box dimension.

However, while a given polymeric film's low oxygen permeability may be a reasonable predictor of the polymeric film's low permeability to the smaller odorous molecules in human fecal matter, such as $H_2S$ and $CH_3SH$, such permeability may not be a reasonable predictor of the polymeric film's permeability to larger molecules, such as DEDS and 3-methyl indole. Hence, the inventors of the present application believe that a given polymeric film's low oxygen permeability does not provide a reasonable predictor of the usefulness of the polymer film in ostomy applications. The permeabilities to $H_2S$, DEDS and 3-methyl indole are selected to predict the odor barrier performance in ostomy applications, as these three compounds represent the main chemical families of odorous compounds found in feces, and cover a range from relatively small to large molecule sizes.

In the present invention, it has been found that polymer films that function as a barrier to molecules having a CMD $\geq$ 0.40 nm can be formed from, but are not limited to, polymeric resins pertaining to Polymer List I. Polymer List I comprises: polymethyl methacrylates (PMMA), PET-G, an amorphous thermoplastic co-polyester resin (e.g. B-100 resin supplied by Mitsui Chemicals Europe GmbH) (hereinafter referred to as "APE-1"), blends of PET-G and such an amorphous thermoplastic co-polyester resin, blends of PET-G and a styrene-butadiene copolymer (PET-G/SB), blends of PET-G and a styrene-butadiene-styrene block copolymer (PET-G/SBS), blends of PET-G and a maleic anhydride (MAH) grafted ethylene-methyl acrylate copolymer (PET-G/MAH-g-EMA), blends of PET-G and an ethylene-methyl acrylate-glycidyl methacrylate copolymer, blends of PET-G and a MAH functionalized styrene-ethylene-butene-styrene (PET-G/SEBS) block copolymer, blends of PET-G and a styrene-isoprene-styrene (PET-G/SIS) block copolymer, and amorphous thermoplastic polyester resins having a glass transition ($T_g$) temperature >50° C., amorphous polyamide or copolymer polyamide having a $T_g \leq 120°$ C., epoxies, amorphous polyurethanes and blends thereof with $\geq 60$ wt % PET-G are especially useful as barriers to molecules having a diameter$\geq 0.40$ nm, with PET-G and PMMA being especially preferred.

When preparing the essentially amorphous, non-chlorinated polymeric barrier films from blends such as exemplified above, the minor blend component need not be amorphous, but may be a semi-crystalline polymer. The definition of amorphous and semi-crystalline polymers can be found in the "Polymer Science Dictionary", 1989 edition, Elsevier Applied Science. It should also be understood that when the essentially amorphous, non-chlorinated polymeric barrier films are prepared from blends such as exemplified above, the major blend component, i.e., PET-G, constitutes $\geq 60$ wt % of the blend. Typical examples of such blends are the following: 1) 70 to 95 wt % of a blend of PET-G and a SB copolymer; 2) 60 to 90 wt % of a blend of PET-G and a SBS block copolymer; 3) 70 to 96 wt % of a blend of PET-G and a MAH-g-EMA copolymer; 4) 70 to 96 wt % of a blend of PET-G and an ethylene-methyl acrylate-glycidyl methacrylate copolymer; 5) 70 to 96 wt % of a blend of PET-G and a MAH functionalized SEBS block copolymer; and 6) 70 to 96 wt % of a blend of PET-G and a SIS copolymer.

Blends of PET-g and an amorphous thermoplastic polyester resin such as APE-1 readily replace PET-G alone. Such blends have an APE-1 content that is desirably 0–100 wt %, preferably 10–80 wt % and more preferably 20–70 wt % and, conversely, a PET-G content that is desirably 100–0 wt %, preferably 90–20 wt % and more preferably 80–30 wt %. In each instance, the percentages total 100 wt %, with all percentages based on blend weight.

It has been found that it is critical that the essentially amorphous, non-chlorinated polymeric barrier films according to the present invention which are a barrier to molecules having a diameter$\geq 0.40$ nm, also possess a $H_2S$ permeation rate of $\leq 60$ cm$^3$/m$^2$-day.

The polymeric barrier films of the present invention which are barrier to molecules having a diameter$\geq 0.55$ nm include, but are not limited to, films formed from Polymer List I and Polymer List II. Polymer List. II comprises: styrene-acrylonitrile (SAN) copolymers, blends of a SAN copolymer and an ethylene-styrene interpolymer (SAN-ESI), acrylonitrile-butadiene-styrene (ABS) terpolymer; impact-modified polymethyl methacrylate (PMMA-IM); polycarbonate (PC); impact-modified polycarbonate (PC-IM); and PC and ABS (PC/ABS) terpolymer alloy.

The polymeric barrier films of the present invention which are barrier to molecules having a diameter$\geq 0.70$ nm include, but are not limited to, films formed from Polymer Lists I, II and III. Polymer List III comprises: polystyrenes, including general purpose polystyrenes (GPPS), high impact polystyrenes (HIPS), blends of GPPS and HIPS (GPPS/HIPS), blends of GPPS and a SB copolymer (GPPS/SB), blends of GPPS and ESI (GPPS/ESI), and blends of GPPS and SIS block copolymer (GPPS/SIS). Amorphous polyamides and co-polyamides having a $T_g > 120°$ C. are not within the scope of the present invention.

Examples of essentially amorphous, non-chlorinated polymeric barrier films prepared from blends of Polymer Lists II or III above may comprise the components of the blend in any proportion, but typically as follows: 1) 60 to 95 wt % of a blend of SAN copolymer and ESI; 2) 30 to 70 wt % of a blend of GPPS and HIPS; 3) 60 to 90 wt % of a blend of GPPS and SB copolymer; 4) 60 to 90 wt % of a blend of GPPS and ESI; and 5) 60 to 90 wt % of a blend of GPPS and SIS block copolymer.

The aforementioned ESI is a substantially random interpolymer comprising in polymerized form i) $\geq$one alpha-olefin ($\alpha$-olefin) monomer and ii) $\geq$one vinyl or vinylidene aromatic monomers and/or $\geq$one sterically hindered aliphatic or cycloaliphatic vinyl or vinylidene monomers, and optionally iii) other polymerizable ethylenically unsaturated monomer(s).

The term "interpolymer" is used herein to indicate a polymer wherein $\geq$two different monomers are polymerized to make the interpolymer.

The term "substantially random" in the substantially random interpolymer resulting from polymerizing i) $\geq$one olefin monomer and ii) $\geq$one vinyl or vinylidene aromatic monomer and/or $\geq$one or more sterically hindered aliphatic or cycloaliphatic vinyl or vinylidene monomers, and optionally iii) other polymerizable ethylenically unsaturated monomer(s) as used herein generally means that the distribution of the monomers of said interpolymer can be described by the Bernoulli statistical model or by a first or second order Markovian statistical model, as described by J. C. Randall in POLYMER SEQUENCE DETERMINATION, Carbon-13 NMR Method, Academic Press New York, 1977, pp. 71–78. Preferably, such substantially random interpolymers do not contain more than 15% of the total amount of vinyl or vinylidene aromatic monomer in blocks of vinyl or vinylidene aromatic monomer >than 3 units. More preferably, the interpolymer is not characterized by a high degree of either isotacticity or syndiotacticity. This means that, in the carbon-13 NMR spectrum of the substantially random interpolymer, peak areas corresponding to the main chain methylene and methine carbons representing either meso diad sequences or racemic diad sequences should not exceed 75% of the total peak area of the main chain methylene and methine carbons. The subsequently used term "substantially random interpolymer" or "SRIP" means a substantially random interpolymer produced from the above-mentioned monomers.

Suitable olefin monomers which are useful for preparing a SRIP include, for example, olefin monomers containing from 2 to 20 ($C_{2-20}$), preferably from 2 to 12 ($C_{2-12}$), more preferably from 2 to 8 ($C_{2-8}$) carbon atoms. Particularly suitable are ethylene, propylene, butene-1, 4-methyl-1-pentene, hexene-1 or octene-1 or ethylene in combination with one or more of propylene, butene-1, 4-methyl-1-pentene, hexene-1 or octene-1. Most preferred are ethylene or a combination of ethylene with $C_{3-8}$-$\alpha$-olefins. These alpha-olefins ($\alpha$-olefins) do not contain an aromatic moiety.

Other optional polymerizable ethylenically unsaturated monomer(s) include strained ring olefins such as norbornene and $C_{1-10}$ alkyl or $C_{6-10}$ aryl substituted norbornenes, with an exemplary interpolymer being ethylene/styrene/norbornene.

Suitable vinyl or vinylidene aromatic monomers, which can be employed to prepare a SRIP, include, for example, those represented by the following Formula I

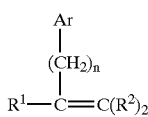

(Formula I)

wherein $R^1$ is selected from the group of radicals consisting of hydrogen and $C_{1-4}$ alkyl radicals, preferably hydrogen or methyl; each $R^2$ is independently selected from the group of radicals consisting of hydrogen and $C_{1-4}$ alkyl radicals, preferably hydrogen or methyl; Ar is a phenyl group or a phenyl group substituted with from 1 to 5 substituents selected from the group consisting of halo, $C_{1-4}$-alkyl, and $C_{1-4}$-haloalkyl; and n has a value from zero to 4, preferably from zero to 2, most preferably zero. Particularly suitable such monomers include styrene and lower alkyl- or halogen-substituted derivatives thereof. Preferred monomers include styrene, α-methyl styrene, the lower ($C_{1-4}$) alkyl- or phenyl-ring substituted derivatives of styrene, such as for example, ortho-, meta-, and para-methylstyrene, t-butyl styrene, the ring halogenated styrenes, such as chlorostyrene, para-vinyl toluene or mixtures thereof. A more preferred aromatic monovinyl monomer is styrene.

The most preferred substantially random interpolymers are interpolymers of ethylene and styrene and interpolymers of ethylene, styrene and ≧one $C_{3-8}$ α-olefin.

The SRIPs usually contain from 0.5 to 65, preferably from 1 to 55, more preferably from 2 to 50 mole percent (mol %) of ≧one vinyl or vinylidene aromatic monomer and/or sterically hindered aliphatic or cycloaliphatic vinyl or vinylidene monomer and from 35 to 99.5, preferably from 45 to 99, more preferably from 50 to 98 mol % of ≧one $C_{2-20}$ aliphatic olefin. SRIPs can be prepared according to WO98/10014 and its US equivalents U.S. Pat. No. 5,703,187 and U.S. Pat. No. 5,872,201, the relevant teachings of which are incorporated herein by reference.

The barrier films of the present invention may contain one or more of the following additives: processing aids, such as fluoropolymers, silicones or siloxanes; inorganic fillers such as barium sulfate, calcium carbonate, mica, silica, silica gel, nanofillers and talc; slip additives such as fatty acid amides; antiblock additives; odor absorbers; humidity absorbers; molecular sieves; pigments; antistatic additives; antifog agents; antioxidants; UV stabilizers; dielectric heating sensitizing additives; pigments; colors; activated carbon; fragrance; nucleating agents, clarifiers; biocides and antimicrobial additives. The additives may optionally be encapsulated in microgranules. At least one outside layer of the film may be subjected to a surface treatment such as corona treatment or flame treatment or plasma treatment to increase its surface tension and improve its printability. Optionally, ≧one surface of the film may also be coated with a thin layer of metal or metal oxide such as aluminum, aluminum oxide, or silicon oxide.

At least one surface of the film can be embossed or texturized to improve resistance to blocking, machinability, or handleability or to impart some performance benefit like softness, suppleness or appearance.

The essentially amorphous, non-chlorinated polymeric barrier films used in accordance with the present invention as barriers to odors and organic molecules may be used as single or monolayer films or as a component film of a multilayer film structure. Examples of the multilayer film structures comprise, but are not limited to, 2 to 7 layers and could, for example, take the form of A/B/D/C/D/E/F or A/B/C/B/A or A/B/C/D/E or A/B/C/D, or A/C/B/, or C/B, with the "C" layer being the essentially amorphous, non-chlorinated polymeric film layer of the present invention, with the other layers comprising adhesive, intermediate or skin layers. Multilayer film structures having more than one "C" layer, i.e., odor barrier layer, are also contemplated.

When the essentially amorphous, non-chlorinated polymeric films are used as single- or monolayer barrier films, the film has a thickness that depends upon the intended end-use of the film as well as the individual odor and organic compound barrier properties of the films. However, the thickness typically ranges from 5 to 50 micrometers (μm), with from 10 μm to 25 μm being more typical, and from 12 μm to 20 μm being most typical. Although any essentially amorphous, non-chlorinated polymeric barrier film useful in the present invention may be used as a monolayer film, multilayer films of essentially amorphous, non-chlorinated polymers are also contemplated.

The monolayer barrier films of the present invention are prepared by conventional techniques, such as by extrusion, blowing, or casting, with extrusion being preferred. The barrier films of the present invention are also non-oriented films.

When not pigmented, not embossed and uncoated, the barrier films of the present invention are also transparent as defined by a haze value ≦45%, measured according to American Society for Testing and Materials (ASTM) test D1003. If haze is not important, the use of one or more of pigment addition, embossing, coating, or inclusion of other additives will not alter the scope of the present invention.

When the essentially amorphous, non-chlorinated polymeric barrier films are used as component films of a multilayer film structures, the essentially amorphous, non-chlorinated polymeric barrier film which provides the odor and organic compound barrier properties to the multilayer film structure typically has a thickness of from 2 μm to 50 μm, with from 3 μm to 35 μm being more typical and is not oriented.

Multilayer film structures typically include ≧one layer formed from a polymer other than that used in the barrier film layer. Selection of such polymer(s) depends upon intended end uses for the multilayer structure. If freedom from chlorine is essential, all layers preferably lack chlorine. In applications where some chlorine is acceptable, such as packaging, protective clothing or soil fumigation, the multilayer film structures may also comprise chlorinated film layers in addition to the essentially amorphous, non-chlorinated polymeric barrier film of the present invention.

Polymers suitable for use in forming non-barrier layers include: LDPE, linear low density polyethylenes (LLDPE), ultra low density polyethylene (ULDPE), homogeneous EAO copolymers, HDPE, PP homo- or copolymers, rubber modified PP, low modulus PP homo- or copolymers, low crystallinity PP homo- or copolymers, syndiotactic PP homo- or copolymers, ethylene-propylene-diene monomer elastomer (EPDM), ethylene-polypropylene rubbers (EPF), substantially linear EAO copolymers, styrene-butadiene copolymers (SB or SBS), SEBS copolymers, styrene-isoprene copolymers (SI or SIS), ethylene-alkyl acrylate copolymers, such as, for example, ethylene-methyl acrylate (EMA), ethylene-butyl acrylate (EBA), ethylene-ethyl acrylate (EEA), ethylene-vinyl acetate (EVA), ethylene-acrylic acid copolymers (EAA), ionomer resins, elastomeric co-polyesters, ethylene-methyl acrylic acid copolymers (EMAA), polynorbornene, ESI, thermoplastic polyurethane (TPU), polyether-amide block copolymers, EVA-carbon monoxide copolymers (EVACO), MAH-modified polyethylene, maleic anhydride modified EVA, MAH-EMA, MAH-EBA, MAH-PP, glycidyl methacrylate modified EMA, glycidyl methacrylate modified EBA, glycidyl methacrylate modified EVA, polyamides, and blends thereof. One such blend includes an amorphous EAO polymer and a low crystallinity PP homo- or copolymer. EP 641,647 and its US equivalent U.S. Pat. No. 5,616,420 as well as EP 527 589, the relevant teachings of which are incorporated herein by reference, disclose, in part, blends of an amorphous polyolefin and a crystalline PP.

The use of copolymers of olefins and polar comonomers will additionally improve the high frequency (HF) sealing properties of the film.

Chlorinated polymers which can optionally be used together with the essentially amorphous, non-chlorine containing barrier films of the present invention include, for example, polyvinyl chloride (PVC), chlorinated polyethylene (CPE), poly(vinylidene chloride) (PVDC), PVDC/VC copolymers (PVDC/VC), PVDC/methyl acrylate copolymers (PVDC/MA), and mixtures thereof.

In a multilayer structure, the polymeric layers located immediately adjacent to the barrier layer will typically function as adhesive or tie layers, while other, non-adjacent layers typically function as intermediate or skin layers. The overall thickness of such a multilayer film structure depends upon the individual film or layer thicknesses. An individual film thickness depends upon a variety of factors, such as ease and cost of manufacturing a film of a given thickness, film physical and chemical properties, and the environment to which the multilayer film structure will be exposed. The overall thickness of such a multilayer film structure typically ranges from 20 µm to 350 µm, with from 30 µm to 200 µm being more typical, and from 40 µm to 150 µm being most typical.

When used in a TDDS application, such as a backing layer for a TDDS article or patch, the multilayer film structures typically have a two or three layer configuration with an overall thickness of 15 to 80 µm, preferably 25 to 50 µm. Such structures typically have an A/B or an A/C/D configuration. Layer A serves as a barrier layer and desirably comprises PET-G, APE-1, a blend of PET-G and APE-1, an amorphous thermoplastic polyester homo- or copolymer resin that has a Tg of at least 50° C., and blends thereof such as a blend of one or both of PET-G and APE-1 with such a resin. Layer A has a thickness of 8–20 µm, preferably 8–15 µm. Layer B comprises an EVA copolymer with a vinyl acetate content of 15–30 wt %, an EMA copolymer with a methyl acrylate content of 15–30 wt % or an EBA copolymer with a butyl acrylate content of 15–30 wt %. Layer C includes all of the copolymers of Layer B plus MAH-g-EVA, MAH-g-EMA, MAH-g-EBA, glycidyl methacrylate grafted EVA, EMA or EBA, ethylene-acrylic ester-MAH terpolymers, ethylene-acrylic ester-glycidyl methacrylate terpolymers, ethylene-glycidyl methacrylate copolymers, SB copolymers, EVACO terpolymers, SI and SIS polymers, and blends thereof, together with. Layer C functions as a tie layer and has a thickness of 2–15 µm. Layer D comprises any of the polymers identified above as suitable polymers for use in forming non-barrier layers other than the polyamides. The EVA, EBA and EMA, when used, preferably have a non-ethylene monomer content of 6–20 wt %. Any or all of layers B, C and D may include one or more of the slip and antiblock additives disclosed herein. In addition, any one or more of layers A–D may include an additive such as an antioxidant, a pigment, a ultraviolet light stabilizer or a processing aid. As with the other multilayer film structures, surface layer treatments may enhance one or more features of those structures having utility in TDDS applications.

Unless otherwise stated, as in the case of <50, each range includes both endpoints that establish the range.

Conventional processes such as blowing or casting, co-extrusion, extrusion coating, extrusion lamination, or adhesive lamination may prepare the multilayer film structures of the present invention.

When used in a monolayer or a multilayer film structure as a barrier to molecules having a diameter≧0.40 nm, the barrier films of the invention have a 3-methyl indole breakthrough time ≧2 hours (hrs), preferably 2–300 hrs, and a DEDS breakthrough time ≧8 minutes (min), preferably 20–1200 min. Such film structures serve as useful barriers to odors and organic molecules.

Table 1 provides representative barrier films useful in accordance with the present invention along with their respective 3-methyl indole and DEDS breakthrough times. Table 1 and succeeding Tables 2–4 are intended to be illustrative only and do not limit scope of the present invention in any way.

TABLE 1

| Film | 3-Methyl Indole Breakthrough Time (hrs)[2] | | | | | | | | | DEDS Breakthrough time (min) 2 | | | | | | | | |
|---|---|---|---|---|---|---|---|---|---|---|---|---|---|---|---|---|---|---|
| | 2 | 4 | 10 | 20 | 40 | 80 | 150 | 200 | 300 | 8 | 20 | 50 | 100 | 150 | 300 | 500 | 1000 | 1200 |
| SAN | Y | Y | Y | Y | Y | Y | Y | Y | N | Y | Y | Y | Y | N | N | N | N | N |
| SAN-ESI | Y | Y | Y | Y | Y | Y | Y | N | N | Y | Y | Y | Y | N | N | N | N | N |
| ABS | Y | Y | Y | Y | Y | Y | N | N | N | Y | Y | Y | Y | Y | N | N | N | N |
| PMMA | Y | Y | Y | Y | Y | Y | Y | Y | Y | Y | Y | Y | N | N | N | N | N | N |
| PMMA-IM[1] | Y | Y | Y | Y | Y | Y | Y | N | N | Y | Y | Y | N | N | N | N | N | N |
| PC | Y | Y | Y | Y | Y | Y | Y | Y | Y | Y | Y | Y | Y | Y | Y | Y | Y | Y |
| PC-IM[1] | Y | Y | Y | Y | Y | Y | Y | Y | N | Y | Y | Y | Y | Y | Y | Y | N | N |
| PC-ABS | Y | Y | Y | Y | Y | Y | Y | N | N | Y | Y | Y | Y | Y | Y | Y | Y | N |
| PET-G | Y | Y | Y | Y | Y | Y | Y | Y | Y | Y | Y | Y | Y | Y | Y | N | N | N |
| PET-G/SB | Y | Y | Y | Y | Y | Y | Y | Y | Y | Y | Y | Y | Y | N | N | N | N | N |
| PET-G/SBS | Y | Y | Y | Y | Y | Y | Y | N | N | Y | Y | Y | N | N | N | N | N | N |
| GPPS/SB | Y | Y | N | N | N | N | N | N | N | Y | Y | N | N | N | N | N | N | N |
| GPPS/ESI | Y | Y | Y | Y | Y | Y | Y | Y | N | Y | Y | Y | Y | Y | N | N | N | N |
| GPPS/SIS | Y | N | N | N | N | N | N | N | N | Y | N | N | N | N | N | N | N | N |
| APE-1/PET-G (50/50%) | Y | Y | Y | Y | Y | Y | N | N | N | Y | Y | Y | Y | Y | N | N | N | N |

[1]IM = Impact modified;
[2]all time entries are > time stated;
Y means breakthrough time exceeds time stated;
N means breakthrough occurs below time stated When used in a monolayer or a multilayer film structure as a barrier to molecules having a diameter≧to 0.40 nm, the barrier films of the invention have a 3-methyl indole breakthrough time ≧2 hrs, preferably 2–300 hrs, and an $H_2S$ breakthrough time ≧40 seconds (secs), preferably 40–250 secs. Such films serve as useful barriers to odors and organic molecules. Table 2 provides representative barrier films useful in accordance with the present invention along with their respective 3-methyl indole and $H_2S$ breakthrough times, wherein the films may be monolayer films or components in a multilayer film structure.

Yet, when used in a monolayer or a multilayer film structure as a barrier to molecules having a diameter $\geq 0.40$ nm, the barrier films of the invention have a DEDS breakthrough time of 8 minutes (min), preferably 8–1200 min, and an $H_2S$ breakthrough time of 40 secs, preferably 40–250 secs. Such films serve as useful barriers to odors and organic molecules. Table 3 provides representative barrier films useful in accordance with the present invention along with their respective DEDS and an $H_2S$ breakthrough times, wherein the films may be monolayer films or components in a multilayer film structure.

Moreover, when used in a monolayer or a multilayer film structure as a barrier to odors, the barrier films have a 3-methyl indole breakthrough time $\geq 2$ hrs, preferably 2–300 hrs, a DEDS breakthrough time $\geq 8$ min, preferably 8–1200 min, and an $H_2S$ breakthrough time $\geq 40$ secs, preferably 40–250 secs.

Table 4 provides representative barrier films useful in accordance with the present invention along with their respective 3-methyl indole, DEDS and an $H_2S$ breakthrough times, wherein the barrier films may be monolayer films or components in a multilayer film structure.

TABLE 2

| | 3-Methyl Indole Breakthrough Time (hrs)[2] | | | | | | | | $H_2S$ Breakthrough Time (secs)[2] | | | | | | |
|---|---|---|---|---|---|---|---|---|---|---|---|---|---|---|---|
| | 2 | 4 | 10 | 20 | 80 | 150 | 200 | 300 | 40 | 100 | 150 | 200 | 250 | 400 | >600 |
| SAN | Y | Y | Y | Y | Y | Y | Y | N | Y | Y | Y | N | N | N | N |
| ABS | Y | Y | Y | Y | Y | N | N | N | Y | N | N | N | N | N | N |
| PMMA | Y | Y | Y | Y | Y | Y | Y | Y | Y | Y | Y | Y | Y | N | N |
| PC | Y | Y | Y | Y | Y | Y | Y | N | Y | N | N | N | N | N | N |
| PC-IM[1] | Y | Y | Y | Y | Y | Y | Y | N | Y | N | N | N | N | N | N |
| PET-G | Y | Y | Y | Y | Y | Y | Y | Y | Y | Y | Y | Y | Y | Y | N |
| APE-1/PET-G (50/50%) | Y | Y | Y | Y | Y | N | N | N | Y | Y | Y | Y | Y | Y | Y |

[1]IM = Impact modified;
[2]all time entries are > time stated;
Y means breakthrough time exceeds time stated;
N means breakthrough occurs below time stated

TABLE 3

| | DEDS Breakthrough Time (min)[2] | | | | | | | | | $H_2S$ Breakthrough Time (secs)[2] | | | | | | |
|---|---|---|---|---|---|---|---|---|---|---|---|---|---|---|---|---|
| | 8 | 20 | 50 | 100 | 150 | 300 | 500 | 1000 | 1200 | 40 | 100 | 150 | 200 | 250 | 400 | >600 |
| SAN | Y | Y | Y | Y | N | N | N | N | N | Y | Y | Y | N | N | N | N |
| ABS | Y | Y | Y | Y | N | N | N | N | N | Y | N | N | N | N | N | N |
| PMMA | Y | Y | Y | N | N | N | N | N | N | Y | Y | Y | Y | Y | N | N |
| PC | Y | Y | Y | Y | Y | Y | Y | Y | Y | Y | N | N | N | N | N | N |
| PC-IM[1] | Y | Y | Y | Y | Y | Y | Y | N | N | Y | N | N | N | N | N | N |
| PET-G | Y | Y | Y | Y | Y | Y | N | N | N | Y | Y | Y | Y | Y | Y | N |
| APE-1/PET-G (50/50%) | Y | Y | Y | Y | Y | N | N | N | N | Y | Y | Y | Y | Y | Y | Y |

[1]IM = Impact modified;
[2]all time entries are > time stated;
Y means breakthrough time exceeds time stated;
N means breakthrough occurs below time stated

TABLE 4

| | 3-Methyl Indole Breakthrough Time (hrs)[2] | | | | | | | | | DEDS Breakthrough time (min)[2] | | | | | | | | |
|---|---|---|---|---|---|---|---|---|---|---|---|---|---|---|---|---|---|---|
| | 2 | 4 | 10 | 20 | 40 | 80 | 150 | 200 | 300 | 8 | 20 | 50 | 100 | 150 | 300 | 500 | 1000 | 1200 |
| SAN | Y | Y | Y | Y | Y | Y | Y | Y | N | Y | Y | Y | Y | N | N | N | N | N |
| ABS | Y | Y | Y | Y | Y | N | N | N | N | Y | Y | Y | Y | N | N | N | N | N |
| PMMA | Y | Y | Y | Y | Y | Y | Y | Y | Y | Y | Y | Y | N | N | N | N | N | N |
| PC | Y | Y | Y | Y | Y | Y | Y | Y | N | Y | Y | Y | Y | Y | Y | Y | Y | Y |
| PC-IM[1] | Y | Y | Y | Y | Y | Y | Y | Y | N | Y | Y | Y | Y | Y | Y | Y | N | N |
| PET-G | Y | Y | Y | Y | Y | Y | Y | Y | Y | Y | Y | Y | Y | Y | Y | N | N | N |
| APE/PET-G (50/50%) | Y | Y | Y | Y | Y | Y | N | N | N | Y | Y | Y | Y | Y | N | N | N | N |

TABLE 4-continued

|  | H$_2$S Breakthrough Time (secs)[2] | | | | | | |
|---|---|---|---|---|---|---|---|
|  | 40 | 100 | 150 | 200 | 250 | 400 | >600 |
| SAN | Y | Y | Y | N | N | N | N |
| ABS | Y | N | N | N | N | N | N |
| PMMA | Y | Y | Y | Y | Y | N | N |
| PC | Y | N | N | N | N | N | N |
| PC-IM[1] | Y | N | N | N | N | N | N |
| PET-G | Y | Y | Y | Y | Y | Y | N |
| APE/PET-G (50/50%) | Y | Y | Y | Y | Y | Y | Y |

[1]IM = Impact modified;
[2]all time entries are > time stated;
Y means breakthrough time exceeds time stated;
N means breakthrough occurs below time stated In addition, depending upon the end-use of the polymeric barrier films of the present invention, it may be desirable that the polymeric barrier films of the present invention or multilayer polymeric film structure having a polymeric barrier film of the present invention as a component film exhibit additional properties.

For example, in addition to barrier properties, it is often desirable that polymeric films not emit noise when crumpled. In ostomy or incontinence applications, it is desirable that the ostomy or incontinence bags not emit noise. However, when crumpled, most polymeric films, especially multilayer polymer films comprised of individual polymeric film layers having different rigidities (i.e., modulus), emit noise. When a reduction in noise is desired, a "noise dampening" polymer may be included, typically in amounts ≧25 wt %, with other (second) polymeric resins to form polymeric films of the present invention having barrier properties. Typically, these polymeric barrier films have a noise level ≦50 decibels (dBA) at one or more octave frequency bands between 1 kilohertz (kHz) and 16 kHz.

In addition, these polymeric resins having quietness properties may be included as component films in multilayer film structures to form multilayer film structures of the present invention having quietness properties. Typically, the noise dampening polymer will be present at ≧30 wt % in the layer and represent ≧25 wt % of the total film composition. Alternatively, a quiet polymeric film may be formed entirely from a noise-dampening polymer and included as a component film in a multilayer film structure of the present invention having quietness properties.

A quiet film according to the present invention will typically be used as a skin or an adhesive layer, but could also be used as an internal layer.

Typically, a noise dampening polymer will have a Tan Δ value ≧0.25 at a temperature within the range between −5° C. and 15° C. or ≧0.32 in the temperature range of from −12° C. to −5° C. Typical noise dampening polymers include, but are not limited to, polynorbornene polymers, low crystallinity PP homo- or copolymers having a heat of fusion <50 Joules/gram (J/g), or syndiotactic PP homo- or copolymers, or atactic PP, or ESI resins. TPUs, EVA copolymers, EMA copolymers, EBA copolymers, PVC, and CPE are not within the scope of this invention with regard to use as noise dampening polymers.

The heat of fusion is determined by differential scanning calorimetry (D.S.C.). The equipment is calibrated using an indium standard. The heat of fusion of PP is determined using a heating rate of +10° C./minute from −50° C. to +220° C. The heat of fusion is integrated between +25° C. and +180° C.

The noise dampening polymer can also be a polymeric composition obtained by blending a polymer which does not have a Tan Δ value ≧0.25 at a temperature within the range between −5 and 15° C. or ≧0.32 at a temperature within the range between −12° C. and −5° C. with at least one of a compatible resin, plasticizer or tackifier that modifies its Tan Δ to such a value. One such blend is the blend of amorphous EAO polymer and a low crystallinity PP. homo- or copolymer noted above.

Examples of such Tan Δ modifications by blending are described in: The Viscoelastic Properties of Rubber Resin Blends: Parts I., II. and III., J. B. Class and S. G. Chu, Journal of Applied Polymer Science, Vol. 30, 805–842 (1985). Light and Stable Resins for Hot-melt Adhesives, P. Dunckley, Adhesives Age, November 1993. A Statistical Approach to Formulating Deep Freeze HMAS, W. J. HONIBALL, J. LEBEZ and al., Adhesives Ages, May 1997, pages 18–26. Tackifier Resins, James A. Schlademan, Handbook of Pressure Sensitive Adhesive Technology, Chapter 20, pages 527–544.

While certain polymers, such as the PP homopolymer and propylene copolymers (PCP-1, PCP-2 and PCP-3) shown in Table 5 below, may provide sufficient noise dampening performance to serve as a sole noise dampening polymer, others require augmentation with at least one other polymer or polymer modifier. In addition, blends of two or more resins serve as effective substitutes for such "sole noise dampening polymers". For example, a blend of an amorphous poly (α-olefin) such as REXTAC® APAO2180, and a 2 melt flow rate random propylene/ethylene copolymer (2.3 wt % ethylene)) approximates one or more of the REXFLEX® flexible polyolefins (FPOs) shown in Table 5. Other blends of a high molecular weight (low melt flow rate) amorphous poly (α-olefin) and a random propylene copolymer also provide effective results. One such blend is marketed by Ube Industries under the trade designation CAP-350. EP 527,589 and its US equivalent U.S. Pat. No. 5,468,807, and EP 641,647 and its US equivalent U.S. Pat. No. 5,616,420, the relevant teachings of which are incorporated herein, disclose such blends in an intermediate layer.

In addition, the use of a noise-dampening polymer or polymer composition is especially advantageous when it is included in a multilayer film structure that contains ≧one other polymeric film layer which has a storage modulus (G') ≧2×10$^4$ Newtons per square centimeter (N/cm$^2$) at room temperature. The polymeric film layers which have a storage modulus (G') ≧2×10$^4$ N/cm$^2$ are typically prepared from amorphous thermoplastic polyesters, such as PET-G, polyethylene terephthalate (PET), polybutylene terephthalate (PBT), and other thermoplastic polyesters, EVOH, PC, polyvinyl alcohol (PVA), SAN, ABS, PMMA, SB copolymers, polyacrylonitrile, polyamides and co-polyamides, such as PA-6, PA-6,6, PA-11, and PA-12, amorphous polyamides, MXD6 polyamide, PVDC, PVDC/VC copolymers, PVDC/MA copolymers, polyhydroxy amino ether copolymers (PHAE), polyurethanes, epoxies, polyethylene naphthalate (PEN), syndiotactic polystyrene, and polystyrene.

Preferred commercially available amorphous thermoplastic polyesters include EASTART™ PETG copolyester 6763 (Eastman Chemical, 1.27 g/cm$^3$ density (ASTM D1505), and 10 cm$^3$-mm/m$^2$-24 hr-atmosphere oxygen permeability (ASTM D3985)) and Mitsui B-100 (Mitsui Chemicals Inc., 1.35 g/cm3 density, Tg of 62° C.). The amorphous thermoplastic polyesters may be used singly or blended together. Using the PETG and B-100 resins by way of example, the blends desirably include from 0 to 100 wt % B-100 and conversely from 100 to 0 wt % PETG. Preferred blends include from 10 to 80 wt % B-100 and 90–20 wt % PETG. More preferred blends include 20 to 70 wt % B-100 and 80–30 wt % PETG. In all instances, the combined resins total 100 wt % and all percentages are based on blend weight. B-100 resin is an amorphous thermoplastic co-polyester resin supplied by Mitsui Chemicals Europe GmbH, it holds the chemical abstracts reference 87365-98-8. This is a copolymer of isophthalic acid (42–48 mole %), terephthalic acid (2–8 mole %), ethylene glycol (>40 mole %) and 1.3-bis (2-hydroxyethoxy)benzene (<10 mole %). The resin has a glass transition temperature of 62° C. and a density of 1.35.

Typically, when the noise dampening polymer or polymer composition is used as part of a multilayer polymeric film structure, it may be present as any of the layers of the multilayer film structure although it is preferred to have it included in a skin layer or in a layer close to an outside surface of the structure.

Although described above in connection with polymeric films having barrier properties, it is understood that the polymeric films having noise dampening characteristics may also be useful in other applications where barrier properties are not required. Thus, another aspect of the present invention is the use of polymers or polymer compositions having a Tan Δ value ≧0.25 at a temperature within the range between −5° C. and 15° C. or ≧0.32 at a temperature within the range of from −12° C. to −5° C. as noise dampening polymeric films or quiet polymeric films.

Further, it may be desirable for the end use application to seal some of the multilayer films described previously, for example, to produce bags. In some instances, the seal strength of some skin polymer compositions may be too low when the film is sealed to itself or to other polymers. A higher seal strength may be obtained by adding a sealant layer as the outermost layer in the film, or by blending into the outermost layer of the film a polymer that improves the seal strength.

EXPERIMENTAL SECTION

I. Barrier Properties

The following developed analytical test methods help quantify barrier properties of the polymeric films of the present invention to oxygen, hydrogen sulfide ($H_2S$) gas, organic sulfides and indoles. DEDS serves as a model organic sulfide compound and 3-methyl indole functions as a model indole compound. Whenever technically possible, permeation testing occurs in high humidity conditions and at 40° C. to more closely simulate the conditions encountered by an ostomy bag in use (i.e., approximating an ostomy bag warmed by body heat and subject to the humidity which exists between human skin and clothing).

The barrier properties of the films to $H_2S$ gas, DEDS and 3-methyl indole are expressed in terms of breakthrough time (B.T.) and/or permeation rate (P.R.). The breakthrough time (B.T.) or time lag, is proportional to the square of the thickness of the barrier resin (*See Polymer Permeability*, pages 11–74, J. Comyn, Elsevier Applied Science Publishers (1985):

B.T.=$T^2$/60D,

Wherein: B.T.=breakthrough time (hrs); T=thickness of film (cm); and D=diffusion coefficient of the permeant in the resin (cm$^2$/sec).

The same reference teaches that permeation rate (P.R) is inversely proportional to the thickness of the barrier resin:

P.R.=P/T, wherein P=resin permeability; and T=thickness of film (cm).

The B.T. represents short-term barrier properties of a product, i.e., before the permeated quantity is high enough to reach the odor threshold of the permeant if the detection is made by the human nose. The B.T. can range from seconds to months depending on the products. The P.R. is more representative of the long-term barrier properties of a product.

The resins used for fabricating the films described in the following examples are listed in Table 5.

TABLE 5

| Resin Name | Type | Supplier | Density | Melt Index (g/10 min) | Other |
|---|---|---|---|---|---|
| AFFINITY* PL 1880 | INSITE* technology polymer (ITP-1) | The Dow Chemical Co. | 0.902 | 1.0[1] | low crystallinity homogeneous copolymer of ethylene and alpha-olefin |
| AFFINITY* KC 8852 | INSITE* technology polymer (ITP-2) | The Dow Chemical Co. | 0.875 | 3.0[1] | low crystallinity homogeneous copolymer of ethylene and alpha-olefin |
| AFFINITY* EG 8100 | INSITE* technology polymer (ITP-3) | The Dow Chemical Co. | 0.870 | 1.0[1] | low crystallinity homogeneous copolymer of ethylene and alpha-olefin |
| ATTANE* 4201 | ULDPE-1 | The Dow Chemical Co. | 0.912 | 1.0[1] | copolymer of ethylene and octene |
| ATTANE* | ULDPE-2 | The Dow | 0.913 | 3.2[1] | copolymer of ethylene |

TABLE 5-continued

| Resin Name | Type | Supplier | Density | Melt Index (g/10 min) | Other |
|---|---|---|---|---|---|
| 4202 | | Chemical Co. | | | and octene |
| ATTANE* 4203 | ULDPE-3 | The Dow Chemical Co. | 0.905 | 0.8[1] | copolymer of ethylene and octene |
| AFFINITY* PF 1140 | ITP-4 | The Dow Chemical Co. | 0.896 | 1.6[1] | low crystallinity homogeneous copolymer of ethylene and alpha-olefin |
| CN 4420 | slip and antiblock masterbatch (ADD-1) | Southwest Chemical | — | — | 4% erucylamide + 4% stearamide + 20% silica in EVA carrier |
| REXFLEX ® FPO WL101 | homopolymer polypropylene (PP) | Huntsman | 0.88 | 14[8] | low crystallinity and low modulus PP, (heat fusion ~25 J/g) |
| REXFLEX ® FPO WL201 | copolymer polypropylene (PCP-1) | Huntsman | 0.88 | 2.8[8] | low crystallinity and low modulus PP (heat of fusion ~20 J/g) |
| REXFLEX ® FPO WL210 | copolymer polypropylene (PCP-2) | Huntsman | 0.88 | 6[8] | low crystallinity and low modulus PP (heat of fusion ~20 J/g) |
| REXFLEX ® FPO WL203 | copolymer polypropylene (PCP-3) | Huntsman | 0.88 | 19[8] | low crystallinity and low modulus PP (heat fusion ~20 J/g) |
| VISTAFLEX ™ 671N | non-crosslinked polypropylene/ ethylene- propylene-diene monomer (PP-EPDM) | Advanced Elastomer Systems | 0.91 | — | — |
| GRIVORY ™ G21 | amorphous co-polyamide (co-PA-1) | EMS Chemie A.G. | 1.18 | — | $T_g$ = 125° C. |
| GRILON ™ F34 | polyamide 6 (PA6) | EMS Chemie A.G. | 1.14 | — | |
| EVAL EP E105 | ethylene vinyl alcohol (EVOH) | Kuraray | 1.19 | 5.5[1] | 44 mol % ethylene |
| GRILON ™ BMFE 4581 | co-polyamide (co-PA-2) | EMS Chemie A.G. | 1.20 | — | $T_g$ = 96° C. |
| GRILON ™ CR9 | polyamide 6-12 (PA 6-12) | EMS Chemie A.G. | 1.10 | — | melt point = 200° C. |
| STYRON* 637 | GPPS-1 | The Dow Chemical Co. | 1.05 | 2.5[2] | |
| STYRON* 686 | GPPS-2 | The Dow Chemical Co. | 1.05 | 2.5[2] | |
| STYRON* 665 | GPPS-3 | The Dow Chemical Co. | 1.05 | 1.5[2] | |
| STYRON* 5192 | high impact polystyrene (HIPS-1) | The Dow Chemical Co. | 1.05 | 4.5[2] | 8.5% rubber |
| STYRON* 492U | HIPS-2 | The Dow Chemical Co. | 1.05 | 3.0[2] | 7.2% rubber |
| PET | biaxially oriented polyethylene terephthalate film, thermal class B (130° C.) medium haze H (PET) | MICEL, France | — | — | 12 microns thick monolayer film |
| B-100 | amorphous thermoplastic co-polyester resin (APE-1) | Mitsui Chemicals Europe GmbH | 1.35 | | $T_g$ of 62° C. |
| EASTAR ™ 6763 | PET-G | Eastman Chemical | 1.27 | Inherent Viscosity = 0.75 | 1,4-benzenedicarboxylic acid, dimethyl ester, polymer with 1,4-cyclohexane-dimethanol and 1,2-ethanediol. Amorphous polyester. |
| FINACLEAR ™ 520 | SBS block copolymer (SBS) | Fina | 1.01 | 7.5[2] | 70 wt % styrene |
| V920 | PMMA | Atohaas | 1.18 | 8[3] | |
| HFI-7 | impact modified polymethyl- methacrylate (PMMA-IM) | Atohaas | 1.17 | 11[3] | |
| CALIBRE* 0201-20 | PC-1 | The Dow Chemical Co. | — | 20[4] | |
| CALIBRE* | PC-2 | The Dow | — | 20[4] | |

TABLE 5-continued

| Resin Name | Type | Supplier | Density | Melt Index (g/10 min) | Other |
|---|---|---|---|---|---|
| 200 | | Chemical Co. | | | |
| CALIBRE* 201-22 | PC-3 | The Dow Chemical Co. | — | 22[4] | |
| CALIBRE* IM 401.11 | impact-modified polycarbonate (PC-IM-1) | The Dow Chemical Co. | — | 11[4] | |
| PULSE* 830 | PC-ABS terpolymer alloy | The Dow Chemical Co. | — | 2.5[3] | |
| K-RESIN KR01 | SB | Philipps Petroleum Chemicals | 1.01 | 8.0[2] | |
| INDEX* DS 201.00 | ESI | The Dow Chemical Co. | — | 1.0[1] | 69 wt % styrene |
| TYRIL* 790 | SAN-1 | The Dow Chemical Co. | — | 9.0[3] | 29 wt % acrylonitrile |
| TYRIL* 100 | SAN-2 | The Dow Chemical Co. | — | 8.0[3] | 25% acrylonitrile |
| MAGNUM* 340 | ABS | The Dow Chemical Co. | — | 2.8[3] | 25% acrylonitrile, 12% rubber |
| ELVAX ® 3165 | EVA copolymer (EVA-1) | DuPont | 0.94 | 0.7 | 18 wt % V.A. |
| ELVAX ® 3174 | EVA copolymer (EVA-2) | DuPont | 0.94 | 8[1] | 18 wt % V.A. |
| ELVAX ® 3190 | EVA copolymer (EVA-3) | DuPont | 0.94 | 2[1] | 25 wt % V.A. |
| ESCORENE ™ 740.16 | EVA copolymer (EVA-4) | EXXON | — | 5.5[1] | 24.5% wt % V.A. |
| BYNEL ® 21E533 | MAH-g-EVA copolymer (MAH-g-EVA-1) | DuPont | — | 7.7[1] | adhesive resin |
| BYNEL ® 3860 | MAH-g-EVA-2 | DuPont | — | 5.7[1] | adhesive resin |
| VECTOR ® 4411 | SIS-1 | Dexco | — | 40[2] | 44% styrene |
| VECTOR ® 4211 | SIS-2 | Dexco | — | 13[2] | 30% styrene |
| LOTRYL ™ 24 MA 005 | EMA | Atochem | — | 0.5[1] | 24 wt % M.A. |
| OREVAC ™ 18613 | MAH-g-EMA | Atochem | — | 3.5[1] | ~28% maleic anhydride |
| LOTADER ™ GMA AX 8900 | ethylene-methyl acrylate-glycidyl methacrylate (EMAGMA) | Atochem | — | 6[1] | |
| LDPE 320 | LDPE-1 | The Dow Chemical Co. | 0.924 | 1.75[1] | |
| LDPE 501 | LDPE-2 | The Dow Chemical Co. | 0.922 | 1.9[1] | |
| SARAN 469 | PVDC | The Dow Chemical Co. | — | — | 80/20 wt % VDC/vinyl chloride copolymer |
| ADMER ™ NF 530 | MAH-g-PE | Mitsui & Co. | — | 4.0 | adhesive resin |
| KRATON ™ FG 1901 X | MAH-g-SEBS | Shell Chemicals | 0.91 | 21.0[6] | 28 wt % styrene, 2 wt % maleic anhydride |
| CPE/EVA blend | blend of 60% chlorinated polyethylene (36 wt % chlorine, .2% residual crystallinity) and 40% EVA (15 wt % vinyl-acetate, melt index of 2.5 @ 190/2.16). | — | — | — | — |
| EVA | EVA | — | — | 0.5 to 5.0 | 15 to 25 wt % vinyl acetate |
| HDPE | any type of HDPE film grade | — | 0.955 to 0.965 | 0.2 to 8.0[1] | — |
| EEA | ethylene - ethyl acrylate | — | — | 0.5 to 5[1] | 15 to 25 wt % ethyl acrylate |
| EMA | ethylene methyl-acrylate | — | — | 0.5 to 5.0 | 15 to 25 wt % methyl acrylate |
| XU73109.01 | PC-4 | The Dow Chemical Company | — | 12.5[5] | — |
| Xu 73114.03 | PC-IM-2 | The Dow Chemical | — | 8.5[4] | — |

TABLE 5-continued

| Resin Name | Type | Supplier | Density | Melt Index (g/10 min) | Other |
|---|---|---|---|---|---|
| LDPE | any type of LDPE film grade | Company — | 0.917 to 0.925 | 0.5 to 8.0[1] | — |
| EAA | ethylene acrylic acid copolymer | The Dow Chemical Company | — | 1.0 to 15.0 | 5 to 10 wt % acrylic acid |
| CN 706 | slip additive concentrate (ADD-2) | Southwest Chemical | — | — | 10% stearamide in EVA resin |
| 100371 | antiblock concentrate (ADD-3) | Ampacet | — | — | 20% silica in polyolefin |
| 100501 | slip antiblock concentrate (ADD-4) | Ampacet | — | — | 15% silica + 5% erucamide in polyolefin |

*Trademark of The Dow Chemical Company
[1] As determined by ASTM D-1238 at 190° C./2.16 kg
[2] As determined by ASTM D-1238 at 200° C./5 kg
[3] As determined by ASTM D-1238 at 230° C./3.8 kg
[4] As determined by ASTM D-1238 at 300° C./1.2 kg
[5] As determined by ASTM D-1238 at 250° C./1.2 kg
[6] As determined by ASTM D1238 at 230° C./5 kg
[7] As determined by ASTM D1238 at 224° C./1.2 kg
[8] As determined by ASTM D1238 at 230° C./2.16 kg

TEST 1

Determination of the Odor Breakthrough Time of Polymer Films to 3-Methyl Indole The method for determining 3-methyl indole breakthrough time is an olfactometric method, similar to the odor transmission test for colostomy bag material described in Appendix G of the British Standard BS 7127, part 101 (1991).

Preliminary Remarks:

3-Methyl indole (skatole) has a very low odor threshold concentration. Values of 0.02 parts per million (ppm) down to 0.0003 parts per billion (ppb) odor threshold detection level in air are reported in the literature. The test must be performed with a test panel of a minimum of 3 people, with 5 testers being ideal.

Objective and Principle:

The objective of this test method is to determine the odor breakthrough time of 3-methyl indole through polymer films. A polymer film is formed into a small pouch, filled with a 3-methyl indole solution, and sealed. Water and the sealed polymeric pouch are placed within a glass bottle and the bottle closed. The bottle is opened at different time intervals, sniffed by a test panel and compared to a reference. The breakthrough time is defined as the time when the average number of testers detects the 3-methyl indole odor in the test bottle.

Equipment sealing equipment, e.g. household heat sealer for freezer bags

1 $cm^3$ automatic pipette 1-liter, wide-mouth bottle with glass stoppers (46/60 mm)

clear glass beads, diameter of approx. 10 mm.

distilled or deionized water laboratory oven regulated at 40° C.±1° C.

A. Preparation of the 3-Methyl Indole Test Solution

3-Methyl indole is almost insoluble in water (0.005 wt % at 20° C.). Prepare the 3-methyl indole solution for the test by dissolving 0.25 grams (g) of 3-methyl indole crystals in 10 milliliters (mL) of ethanol, and then adding 100 mL of distilled water. The resultant solution has a concentration of 2.27 grams per liter (g/L) of 3-methyl indole.

B. Test Procedure

1. Cut a piece of polymer film of dimensions of approx. 220 mm × 120 mm, fold it lengthwise and seal two sides to make a pouch.
2. Carefully fill the pouch with 1 mL of the 3-methyl indole solution using the pipette, ensuring that no 3-methyl indole solution is dripped onto the seal area or on the outside of the film. Seal the pouch. The dimensions of the finished pouch within the sealed area are 100 mm × 100 mm.
3. About 1 hour in advance of testing, prepare a pouch from a film having a very low barrier to 3-methyl indole (e.g., a 15 μm to 40 μm thick LDPE or HDPE film), using the procedures of 1 and 2 above. Fill the pouch with 1 mL of the 3-methyl indole solution. This pouch shall be used as the reference odor rating value of 5.
4. Prepare a pouch from the film to be tested, or with a film having no marked odor of its own (e.g., polyethylene) and fill with 1 mL of a water/ethanol mixture (10/1 solution). This pouch shall be used as the reference odor rating value of 1.
5. Fill the glass bottles with 2 layers of glass beads. Add some water, but do not submerge the glass beads.
6. Place a sealed pouch in each glass bottles. Put some grease on the glass stopper, close the bottles, and place them in an oven at 40° C.
7. At defined intervals, take the bottles out of the oven and let the individual members of the test panel evaluate the smell in each bottle. Give the smell a relative rating values from 1 to 5, 1 being no smell or neutral/polymeric odor (reference film with water), 2 being 3-methyl indole odor very low but detected, and 5 being very odorous (reference film with 3-methyl indole solution). The time interval is dependent on the breakthrough time of the film, e.g., 1 to 4 hours for short times, and up to 1–4 days for long times. Calculate the average odor rating of the film.

-continued

8. Continue the test until the average odor rating of the film is ≧ 2.
9. For each film, plot the odor rating (arithmetic average of all testers) versus time. The breakthrough time is defined as the time required to reach an average odor rating of 2. This value is obtained by linear interpolation.

More than one sample can be tested at the same time, but it is not recommended to go above 6 or 7 at a time. All testers can smell the same bottles, but care must be taken to let these open the shortest possible time. The same bottles can also be used for the different testing times. It is important to smell the different bottles in the order of increasing odor rating. Smelling a very odorous bottle (like the one with the film rated 5) at the beginning of a series tends to anaesthetize/ saturate the sense of smell and can lead to lower odor ratings. The bottle with the odor reference 5 must be sniffed only at the end of a series and last. The odor rating is the arithmetic average of the ratings of the different testers. If range values greater than 2 within the individual data are found, look closely for an outlier and eliminate it from the calculation whenever possible.

TEST 2

Oxygen Permeability of Polymeric Films

Measure oxygen permeability of the films using an OX-TRAN 10–50 oxygen permeability tester available from Modern Controls Inc. (Minneapolis, Minn., USA) using the ASTM 3985–81 test method at 23° C., and 65–70% relative humidity.

Table 6 shows the oxygen permeability and the 3-methyl indole breakthrough times of a series of polymeric films. The films in Comparative Examples (Comp Ex) number A–F are currently used in ostomy bag applications. The films of the various Examples (Ex) designated with an Arabic numeral represent the present invention. Comp Ex M is a plain polyethylene (PE) film and has the shortest 3-methyl indole breakthrough time of all examples, since PE has very little barrier properties to 3-methyl indole, this film was used as the odor reference 5 in the 3-methyl indole breakthrough time test method. The other examples have higher breakthrough times due to the presence of a "barrier resin" in their structure. The resins used for the fabrication of these films are listed in Table 5.

TABLE 6

| Ex or Comp. Ex. | Film Description | Barrier Layer | Barrier Layer Thickness (μm) | Total Film Thickness (μm) | Oxygen Permeability (cm3/m2 · day · atm) | 3-Methyl Indole B.T. (hours) |
|---|---|---|---|---|---|---|
| A | LDPE/EVA/PVDC/EVA/LDPE | PVDC | 5.5[1] | 70 | 13 | 7 |
| B | LDPE/EVA/PVDC/EVA/LDPE | PVDC | 10.1[2] | 75 | 4.5 | 24 |
| C | CPE/EVA/PVDC/EVA | PVDC | 9.1[3] | 100 | 6 | 65 |
| D | CPE/EVA/PVDC/EVA | PVDC | 10 | 75 | 7.5 | 50 |
| E | EVA/MAH-g-EVA-2/co-PA-1/MAH-g-EVA-2/EVA | amorphous co-PA | 6.2[4] | 70 | 42 | 20 |
| F | EVA/MAH-g-EVA-2/co-PA-1/MAH-G-EVA-2/EVA | amorphous co-PA | 10.2[5] | 70 | 30 | >50 |
| G | EVA/MAH-g-PE/EVOH/MAH-g-PE/EVA | EVOH | 7 | 60 | 14 | 1/4.5[6] |
| H | LDPE/5 μm adhesive/PA6 | PA6 | 18 | 70 | 41 | <2 |
| I | 50 μm LDPE/10 μm adhesive/PA6-12 | PA 6-12 | 25 | 85 | 76 | <2 |
| J | LDPE-1/MAH-g-EVA-2/co-PA-2 4581/MAH-g-EVA-2/LDPE-1 | co-PA | 5.2 | 93 | 6.9 | 3 |
| 1 | LDPE-10/EVA/50:50 GPPS-1 and HIPS-1/EVA/LDPE-1 | 50/50 blend of GPPS and HIPS | 10 | 100 | 1625 | 85 |
| 2 | LDPE/MAH-g-EVA-2/SAN-2/MAH-g-EVA-2/LDPE | SAN | 35 | 85 | 1360 | 200 |
| 3 | LDPE/MAH-g-EVA-2/PMMA/MAH-g-EVA-2/LDPE | PMMA | 35 | 85 | 138 | 390 |
| 4 | 50:50 GPPS-2 and HIPS-2[7] | 50/50 blend of GPPS/HIPS | 19 | 19 | >2000 | >1490 |
| K | LDPE coated with 10 μm cationic epoxy lacquer[8] | cationic epoxy resin | 10 | 100 | 44 | 1 |
| L | coextruded film with EAA skins and 4.5 μm polyhydroxyamino-ether resin | polyhydroxy-aminoether | 4.5 | 24 | 72 | <1 |
| M | HDPE (Reference Film with odor rating = 5) | — | | 15 | >2000 | <0.3 |
| 5 | PETG | PET-G | 18 | 18 | 390 | >388 |
| 6 | LDPE/EVA/ABS/EVA/LDPE | ABS | 6 | 75 | 2260 | ~85 |
| 7 | LDPE/EVA/75:25 PET-G and SBS/EVA/LDPE | 75:25 blend of PET-G and SBS | 7.3[11] | 80 | 712 | 160 |
| 8 | LDPE 501/MAH-g-EVA-2/V920/MAH-g-EVA-2/LDPE | PMMA | 5 | 75 | 665 | >175 |
| 9 | LDPE-2/MAH-g-EVA-2/PMMA-IM/MAH-g-EVA-2/LDPE-2 | impact-modified | 10 | 75 | 607 | 175 |

TABLE 6-continued

| Ex or Comp. Ex. | Film Description | Barrier Layer | Barrier Layer Thickness (μm) | Total Film Thickness (μm) | Oxygen Permeability (cm3/m2 · day · atm) | 3-Methyl Indole B.T. (hours) |
|---|---|---|---|---|---|---|
| 10 | LDPE-2/EEA/PC/EEA/LDPE-2[12] | PMMA PC[13] | 9.0[14] | 75 | 1740 | >147 |
| 11 | LDPE-2/MAH-g-ETA-2/PC-IM-2/MAH-g-EVA-2/LDPE-2[15] | impact modified PC | 5.7[16] | 75 | 2375 | ~270 |
| 12 | LDPE-2/EVA/PC-ABS/EEA/LDPE-2 | PC/ABS alloy | 3.0 | 75 | 4390 | 185 |
| 13 | LDPE-2/EVA/70:30 PET-G and SB/EVA/LDPE-2 | 70:30 blend of PET-G and SS | 10 | 75 | 962 | >147 |
| N | PET[17] | PET | 13 | 13 | 141 | 175 |
| 14 | LDPE-2/EVA/70:30 GPPS-3 and SB/EVA/LDPE-2 | 70:30 blend of GPPS and SB | 10 | 75 | 3865 | 4 |
| 15 | LDPE-2/EVA/PC-1/EMA/LDPE-2[18] | PC | 7.4 | 75 | 1995 | –315 |
| 16 | LDPE-2/EVA/85:15 PET-G and SB/EVA/LDPE-2[19] | 85:15 blend of PET-G and SB | 4.5[20] | 75 | 1070 | >147 |

[1]represents an average between 4.0 μm and 7.1 μm
[2]represents an average between 10.0 μm and 10.2 μm
[3]represents an average between 9.7 μm, 8.0 μm, and 9.6 μm
[4]represents an average between 6.0 μm and 6.4 μm
[5]represents an average between 10.0 μand 10.4 μm
[6]the second value is with no water in the glass bottle to simulate a dry environment
[7]biaxially oriented polystyrene film
[8]cationic epoxy lacquer is GQ26290F from B.A.S.F
[9]cast film
[10]same film structure as used in Ex 29 in Table 7
[11]represents an average between 6.0 μm and 8.6 μm
[12]same film structure as used in Ex 36 in Table 7
[13]80 melt flow rate grade from The Dow Chemical Co.
[14]represents an average between 7.9 μm and 10.0 μm
[15]same film structure as used in Ex 39 in Table 7
[16]represents an average between 5.6 μm and 5.8 μm
[17]biaxially oriented monolayer polyethylene terephthalate (PET) same film structure as used in Comparative Ex N in Table 8
[18]same film structure as used in Ex 35 in Table 8
[19]same film structure as used in Ex 30 in Table 8
[20]represents an average between 4.3 μm and 4.6 μm The data in Table 6 demonstrate that the films currently used in ostomy bag applications (Comp Ex A–F) have 3-methyl indole breakthrough times ≧7 hrs. The EVOH coextruded film of Comp Ex G, which has been suggested for ostomy application, has a 3-methyl indole breakthrough time of 1 hour, making it undesirable for ostomy applications, despite an oxygen permeability comparable to the films of Comp Ex A–F.

The films of Comp Ex H, I, J, K, and L exhibit low oxygen permeability, but 3-methyl indole breakthrough times ≦3 hrs. The films of Ex 2, 4, 5, 6, 15, and 16 exhibit high oxygen permeability, but have 3-methyl indole breakthrough times ≧85 hrs. Therefore, the data of Table 6 clearly demonstrate that no relationship exists between the oxygen permeability of a polymeric film and breakthrough times for 3-methyl indole. The polymers which are essentially glassy at the testing temperature (i.e., PET-G, PET-G/SB and PET-G/SBS blends, PMMA, impact modified PMMA, PS/HIPS blends, SAN, PC, impact modified PC, PC/ABS alloy, ABS, and SAN) surprisingly provide the best barrier properties to 3-methyl indole.

TEST 3

Organic Sulfide (DEDS) Barrier Properties

The method for determining DEDS breakthrough time uses a permeation cell and a mass spectrometry detector. Use a system consisting of a permeation cell, a flow-through hollow fiber membrane and a mass selective detector (MSD) to measure DEDS odor permeation rates across polymer films.

Instrumentation

The permeation cell is two stainless steel disks each having a machined cavity on one face. Also on the face of the disk is an o-ring seating surface. The O-rings are KALREZ® perfluoroelastomer parts (DuPont Dow Elastomers L.L.C.). A polymer film, when clamped between the two disks, defines the upstream and downstream cavities. The upstream cavity contains the permeant. Helium is swept through the downstream cavity and to the detector. The flow rate of the helium is approximately 4 mL/min. The exposed film surface area is 7.3 cm$^2$ and the volume of each cavity is approximately 4 mL. The two sides of the cell are clamped together using plates with seats to center the two halves of the cell. Four bolts are tightened to ensure a seal between the O-rings and the test film.

Use a flow-through hollow fiber silicone membrane to concentrate the permeant due to selectivity of the membrane. Place the permeation cell and the hollow-fiber membrane in a HP5890 Series II Gas Chromatograph (GC) which is held at 40° C. for the permeation test. Plumb the hollow fiber to the transfer line for the mass selective detector (MSD). The conditions for the MSD are listed below:

Instrument: Hewlett Packard 5971A MSD

| Low mass: | 50 | High mass: | 200 |
|---|---|---|---|
| EMV offset: | 0 | Voltage: | 2235 |
| Threshold: | 250 | Mode: | Scan |
| Tune file: | ATUNE | | |

Experimental Procedure

Load the film to be tested onto the bottom half of the cell. Protect the test film from the permeant solution by covering the test film with a piece of LDPE film (approx. 25 μm thick). Place the top half of the cell on the LDPE film and bolt the cell together. Place the cell in the GC with helium flowing through the bottom half of the cell to the hollow fiber membrane.

The permeant solution used for these experiments is 1 mL DEDS/10 mL ethanol (EtOH) (approximately 9 wt % DEDS). Place a three mL aliquot of the solution in the top half of the cell. Data collection begins once the solution is in contact with the film. Continue experiments until steady-state permeation is achieved or for 24 hrs. The breakthrough time is defined as the time at which the detector signal for ion mass 122 reaches an abundance of 6000 counts.

The effect of the LDPE film on the permeation kinetics of the test film is negligible. Breakthrough time of the polyethylene film, determined to be five min, is an insignificant length of time compared to the breakthrough times of the test films. The LDPE film protects the test film from the EtOH. If the skin layers of the film are polar in nature, such as EVA, the EtOH can plasticize the skin layers and effect the integrity of the film as a whole.

The ion at m/z=122 is characteristic of DEDS. Choose this ion because it has one of the highest relative abundances of the fragment ions in the mass spectrum for DEDS. Also it is of high enough molecular weight so as to have minimal interference from other species present in the system.

The abundance is a relative number as the units are arbitrary and depend on the system. Calibrate the system using the calibration gas present in the mass spectrometer as the tune gas. Tune the system prior to running the samples and retune it as necessary.

Table 7 shows the DEDS breakthrough time and the steady state relative permeation rate of a series of polymeric films. These films contain different polymer resins as the barrier layer. The films of Comp Ex A, B, C, E, F, O are currently used in ostomy applications. The resins used for the fabrication of these films are listed in Table 5.

TABLE 7

| Comp Ex/Ex No. | Film Structure | Barrier Layer | Barrier Layer thickness (micron) | DEDS B.T. (min.) | DEDS relative permeation rate (relative unit) |
|---|---|---|---|---|---|
| A | LDPE/EVA/PVDC/EVA/LDPE | PVDC | 5.5[1] | 71 | 450 |
| B | LDPE/EVA/PVDC/EVA/LDPE | PVDC | 10.1[2] | 136 | 200 |
| C | CPE/EVA/PVDC/EVA | PVDC | 9.1[3] | 139 | >350 |
| O | LDPE/EVA/PVDC/EVA/LDPE | PVDC | 4.8 | 47 | 500 |
| E | EVA/MAH-g-EVA-2/GRIVORY G21/MAH-g-EVA-2/EVA | amorphous co-PA | 6.2[4] | 226 | 120 |
| F | EVA/MAH-g-EVA-2/co-PA-1/MAH-g-EVA-2/EVA | amorphous co-PA | 10.2[5] | 190 | 250 |
| M | LDPE | Reference Sample (rating 5) | 25 | 5 | 6000000 |
| 17 | LDPE-1/EVA/70:30 blend of GPPS-1 and ESI/EVA/LDPE-1 | 70:30 blend of GPPS and ESI | 4.6 | 129 | 1000 |
| 18 | LDPE-1-/EVA/70:30 blend of GPPS-3 and ESI/EVA/LDPE-1 | 70:30 blend of GPPS and ESI | 8.4 | 193 | >600 |
| P | LDPE-2/EVA/70:30 blend of GPPS-3 and SIS-1/EVA/LDPE-2 | 70:30 blend of GPPS and SIS | 5.6 | 8 | >4500 |
| 19 | LDPE-2/EVA/70:30 blend of GPPS-3 and SB/EVA/LDPE-2 | 70:30 blend of GPPS and SB | 12.2 | 30 | 1400 |
| 20 | LDPE-2/EVA/70:30 blend of SAN-1 and ESI/EVA/LDPE-2 | 70:30 blend of SAN and ESI | 8.1 | 116 | ~350 |
| 21 | LDPE-2/MAH-g-EVA-2/SAN-2/MAH-g-EVA-2/LDPE-2[6] | SAN | 10.2[7] | 142 | 700 |
| 22 | LDPE-2/MAH-g-EVA-2/SAN-2/MAH-g-EVA-2/LDPE-2 | SAN | 11.2 | 125 | 450 |
| 23 | LDPE-2/MAH-g-EVA-2/PMMA/MAH-g-EVA-2/LDPE-2[8] | PMMA | 11.4 | 82 | 350 |
| 24 | LDPE-2/MAH-g-EVA-2/PMMA-IM/MAH-g-EVA-2/LDPE-2 | PMMA-IM | 8.9 | 77 | 500 |
| 25 | LDPE-1/EVA/ABS/EVA/LDPE-1 | ABS | 7.1 | 112 | 500 |
| 26 | LDPE-1/EVA/ABS/EVA/LDPE-1 | ABS | 16.5 | 169 | 450 |
| 27 | LDPE-2/MAH-g-EVA-2/PET-G/MAH-g-EVA-2/LDPE-2 | PET-G | 8.1 | 166 | 65 |
| 28 | LDPE-2/MAH-g-EVA-2/PET-G/MAH-g-EVA-2/LDPE-2 | PET-G | 10.4 | 187 | 80 |

TABLE 7-continued

| Comp Ex/Ex No. | Film Structure | Barrier Layer | Barrier Layer thickness (micron) | DEDS B.T. (min.) | DEDS relative permeation rate (relative unit) |
|---|---|---|---|---|---|
| 29 | LDPE/EVA/75:25 blend of PET-G and SBS/EVA/LDPE[9] | 75:25 blend of PET-G and SBS | 7.3[10] | 70 | 250 |
| 30 | LDPE-2/EVA/85:15 blend of PET-G and SB/EVA/LDPE-2[11] | 85:15 blend of PET-G and SB | 4.5[12] | 92 | 85 |
| 31 | LDPE-2/EVA/85:15 blend of PET-G and SB/EVA/LDPE-2 | 85:15 blend of PET-G and SB | 9.4 | 119 | — |
| 32 | LDPE-2/EVA/70:30 blend of PET-G and SB/EVA/LDPE-2 | 70:30 blend of PET-G and SB | 8.1 | 115 | >90 |
| 33 | LDPE-2/EEA/PC-4/EEA/LDPE-2 | PC | 4.8 | 800 | >45 |
| 34 | LDPE-2/EMA/PC-1/EMA/LDPE-2 | PC | 5.8 | 1105 | >18 |
| 35 | LDPE-2/EMA/PC-1/EMA/LDPE-2[13] | PC | 7.4 | 1315 | — |
| 36 | LDPE-2/EEA/PC/EEA/LDPE-2[14] | PC[15] | 9.0[16] | >1440 | — |
| 37 | LDPE-2/MAH-g-EVA-1/PC-IM-1/MAH-g-EVA-1/LDPE-2 | impact modified PC | 4.6 | 615 | >400 |
| 38 | LDPE-2/EEA/PC-IM-2/EEA/LDPE-2 | impact modified PC | 7.9 | 916 | >55 |
| 39 | LDPE-2/MAH-g-EVA-2/PC-IM-2/MAH-g-EVA-2/LDPE-2[17] | impact modified PC | 5.7[18] | 455 | 150 |
| 40 | LDPE-2/EEA/PC-ABS/EEA/LDPE-2 | PC-ABS alloy | 15 | 1180 | >30 |
| 41 | LDPE-2/MAH-g-EVA-2/PET-G/MAH-g-EVA-2/LDPE-2 | PET-G | 9.2 | 188 | 72 |
| 42 | LDPE-2/MAH-g-EVA-2/PET-G/MAH-g-EVA-2/LDPE-2 | PET-G | 5.2 | 273 | 40 |
| 43 | LDPE-2/MAH-g-EVA-2/PET-G/MAH-g-EVA-2/LDPE-2 | PET-G | 7.4 | 312 | 33 |

[1]represents an average of 4.0 μm and 7.1 μm
[2]represents an average of 10.0 μm and 10.2 μm
[3]represents an average of 9.7 μm, 8.0 μm, and 9.6 μm
[4]represents an average of 6.0 μm and 6.4 μm
[5]represents an average of 10.0 μm and 10.4 μm
[6]same film structure as used in Ex 51 in Table 8
[7]represents an average of 9.4 μm and 11.0 μm
[8]same film structure as used in Ex 52 in Table 8
[9]same film structure as used in Ex 7 in Table 6
[10]represents an average of 6.0 μm and 8.6 μm
[11]same film structure as used in Ex 16 in Table 6
[12]represents an average of 4.3 μm and 4.6 μm
[13]same film structure as used in Ex 15 in Table 6
[14]same film structure as used in Ex 10 in Table 6
[15]80 melt flow rate grade from The Dow Chemical Co.
[16]represents an average of 7.9 μm and 10.0 μm
[17]same film structure as used in Ex 11 in Table 6
[18]represents an average of 5.6 μm and 5.8 μm Table 7 demonstrates that films currently used for ostomy applications (Comp Ex A, B, C, E, F, O) have a DEDS breakthrough time of approximately 47 minutes or higher, and a DEDS relative permeation rate of 500 or lower. With the exception of the film of Comp Ex P, which has a DEDS breakthrough time of 8 min and a DEDS P.R. of >4500, the films of the present invention (i.e., Ex 17–43) have DEDS breakthrough times and P.R.s in the same range or better than the values for the films currently used for ostomy applications for comparable values of barrier resin thickness. The film of Ex 19 (GPPS-SB blend) has a DEDS breakthrough time slightly lower than 47 min and the films of Ex 17 and 18 (PS-ESI blend) have a DEDS P.R. higher than 500. However, a slight increase in barrier layer thickness should be sufficient to bring these values to the level of the films of Comp Ex A, B, C, E, F, O.

Table 7 further demonstrates that many amorphous polymers or blends are able to provide similar or better protection against the permeation of DEDS and 3-methyl indole relative to traditional barrier polymers such as those in Comp Ex A, B, C, E, F, O. The film of Comp Ex M, which is a pure LDPE film, demonstrates that LDPE has very little barrier properties to DEDS and therefore does not contribute to the barrier properties of the other examples.

TEST 4

Hydrogen Sulfide $H_2S$ Gas Barrier Properties

Measure the permeability of the films to $H_2S$ gas at 40° C., using a permeation cell coupled to a PDHID (Photodiode Helium Ionization Detector) as described below:

Place a piece of film in a permeation cell. Control the temperature of the test cell at 40° C. Flow pure helium gas on one side of the film, while flowing a mixture of 1 wt % $H_2S$ in helium on the other side of the film. Pass the flow of the pure helium gas through a PDHID detector connected to a data acquisition system that records the $H_2S$ concentration in the gas stream as a function of time. Determine the $H_2S$ breakthrough time and the steady state permeation rates on the time/concentration curve. Calibrate the system with a $H_2S$ gas mixture of known concentration.

Table 8 shows the $H_2S$ breakthrough time and the steady state permeation rate of a series of polymeric films. These films contain different polymer resins as the barrier layer. The film of Comp Ex C is currently used in ostomy applications. The resins used for the fabrication of these films are listed in Table 5.

TABLE 8

| Com Ex/Ex. No. | Film Structure | Barrier Layer | Barrier Layer Thickness (μm) | $H_2S$ B.T. (sec) | $H_2S$ Permeation Rate (cm³/day · m²) |
|---|---|---|---|---|---|
| C | CPE/EVA/PVDC/EVA | PVDC | 9.1 | 450 | 3.55 |
| 44 | LDPE-2/MAH-g-EVA-2/PC/MAH-g-EVA-2/LDPE-2 | PC | 6.0 | 68 | 192 |
| 45 | LDPE-2/MAH-g-EVA-2/PET-G/MAH-g-EVA-2/LDPE-2 | PET-G | 8.0 | 263 | 24.3 |
| 41 | LDPE-2/MAH-g-EVA-2/PT-G²/MAH-g-EVA-2/LDPE-2 | PET-G | 9.2 | 155 | 34.0 |
| 46 | LDPE-2/MAH-g-EVA-2/PC-IM-2³/MAH-g-EVA-2/LDPE-2 | impact modified PC | 6.0 | 65 | 168 |
| 47 | LDPE-2/MAH-g-EVA-2/PC-IM-1/MAH-g-EVA-2/LDPE-2 | impact modified PC | 4.6 | 73 | 162 |
| 48 | LDPE-2/MAH-g-EVA-2/ABS/MAH-g-EVA-2/LDPE-2 | ABS | 6.0 | 65 | 116 |
| 49 | LDPE-1/EVA/HIPS-1/EVA/LDPE-1 | HIPS | 10 | 53 | 162 |
| 21 | LDPE-2/MAH-g-EVA-2/SAN-2/MAH-g-EVA-2/LDPE-2 | SAN | 10.2 | 195 | 70 |
| 23 | LDPE-2/MAH-g-EVA-2/PMMA/MAH-g-EVA-2/LDPE-2 | PMMA | 11.4 | 275 | 8.2 |
| N | PET | PET | 13 | 185 | 10.9 |

[1] represents an average of 9.7 μm, 8.0 μm, and 9.6 μm
[2] 5 PET-G layers separated by a layer of adhesion resin. The total thickness of these 5 PET-G layers is reported in Table
[3] represents an average of 9.4 μm and 11.0 μm Table 8 shows that the films used in Ex 41 and 45, with a PET-G barrier layer, and the film used in Ex 23, with a PMMA barrier layer, have $H_2S$ breakthrough times and P.R.s in the same magnitude as a film currently used for ostomy application (Comp Ex C). The film of Ex 21 has an $H_2S$ breakthrough time of about half of that of the film used in Comp Ex C and 20 times its P.R. The film of Comp Ex N (PET) has a P.R. 3 times higher and an $H_2S$ breakthrough time approximately half of that of the film of Comp Ex C.

PET is a semi-crystalline polyester with a melting point of approximately 255° C. and therefore must typically be processed at an extrusion temperature of 270° C. to 290° C. PET-G (Ex 41 and 45) is an essentially amorphous polyester with a Tg of approximately 81° C. and can therefore be processed at lower extrusion temperatures of 190° C. to 220° C. This extrusion temperature range is closer to the temperatures typically used for extruding polyolefins and elastomers. Therefore, it is much easier to coextrude PET-G with these resin families compared to PET ("Film Extrusion Manual", Chapter 19G: Polyester, page 533, TAPPI Press 1992). PET-G also has a lower modulus of elasticity and a higher impact resistance than PET (Eastman Chemical product literature, ref. PPM-204 (May 1996) lists following values: Flexural Modulus=2,100 megapascals (MPa) versus 2,500 MPa; Izod impact strength =102 J/m versus 51 J/m for PET-G copolyester versus PET homopolymer). Therefore, films with a low rigidity (i.e., high flexibility) are more easily achieved with PET-G than with PET. The films used in Ex 44 and 47–50 have $H_2S$ breakthrough times 7 times shorter and P.R.s 33 to 47 times higher than the film of Comp Ex C.

Based upon this data, it is believed that PET-G and PMMA have a good combination of odor barrier properties for small molecules (e.g., $H_2S$ 0.40 nm molecular diameter), larger molecules (e.g., DEDS 0.58 nm molecular diameter) and large molecules (e.g. 3-methyl indole 0.78 nm molecular diameter). Therefore, they are well-suited for ostomy bag applications. The other amorphous polymers (i.e., PC, impact modified PC, ABS, SAN, PS, and blends) have good barrier properties to molecules with a molecular diameter of approximately 0.58 nm and higher (DEDS and 1- or 3-methyl indole), but are not as well-suited for ostomy applications due to their low barrier properties to small molecules (e.g., $H_2S$). Therefore, these polymers are useful for applications where barriers to only larger molecules (e.g., DEDS and 3-methyl indole) are required. For example, in the packaging of odorous chemicals, in protective clothing applications and in trans-dermal drug delivery systems (TDDS).

TEST 5

1% Secant Modulus and Oxygen Permeability of PET-G Blends

As described previously, the PET-G resin can be blended with softer polymers in order to increase its softness and resistance to flex-cracking. For example, compound the PET-G resin listed in Table 5 with 25 wt % of a softer polymer resin in a ZSK-30 compounder. Let the compounded pellets down at 32 wt % and 64 weight percent with pure PET-G resin and feed it into a 30 mm diameter 24 L/D extruder. Extrude monolayer cast films of 30 μm and 60 μm thicknesses through a 250 mm wide die. Measure the 1% secant modulus and oxygen permeability of these films and report the data in Table 9.

TABLE 9

| Flexible Resin | % Flexible Resin in PET-G Film | Oxygen Permeability (cm³/m²-day-atm for 10 μm of resin) | 1% modulus (MPa) (average of MD & TD) |
|---|---|---|---|
| SIS-2 | 0 | 698 | 1682 |
| SIS-2 | 8 | 896 | 1442 |
| SIS-2 | 16 | 1229 | 1316 |
| MAH-g-EMA | 0 | 698 | 1682 |
| MAH-g-EMA | 8 | 989 | 1328 |
| MAH-g-EMA | 16 | 1115 | 1061 |
| EMAGMA | 0 | 698 | 1682 |
| EMAGMA | 8 | 900 | 1411 |

TABLE 9-continued

| Flexible Resin | % Flexible Resin in PET-G Film | Oxygen Permeability (cm³/ m²-day-atm for 10 µm of resin) | 1% modulus (MPa) (average of MD & TD) |
|---|---|---|---|
| EMAGMA | 16 | 1162 | 1092 |
| MAH-g-SEBS | 0 | 698 | 1682 |
| MAH-g-SEBS | 8 | 1040 | 1405 |
| MAH-g-SEBS | 16 | 970 | 1390 |

The data in Table 9 show that it is possible to reduce the modulus of a PET-G resin by blending with a more flexible resin. This allows the production of a less rigid film if high modulus is problematic. On the other hand, the blend has an oxygen permeability greater than that of the PET-G resin. Although the oxygen permeability is not an accurate predictor for the permeability of the film to other gases and chemical compounds, it is believed that, for the same polymer type, the relative variations of oxygen permeability can be useful in predicting the relative variations of permeability and B.T. to other gases and chemical compounds. For example, films of Ex 27 and 32 of Table 7 contain a barrier layer of 8.1 µm pure PET-G (Ex 27) and of 8.1 µm of a 70/30 wt % blend of PET-G/SB (Ex 32). Report the permeabilities to oxygen and DEDS of these two films in Table 10.

TABLE 10

| Ex No. | Oxygen Permeability (cm³/m²-day-atm) at 23° C. | DEDS B.T. (min) | DEDS relative permeation rate (cm³/day-m²) |
|---|---|---|---|
| 27 | 467 | 166 | 65 |
| 32 | 675 | 115 | >90 |

The oxygen permeability of the film of Ex 32 containing the PET-G blend is 45% higher than the pure PET-G resin film of Ex 27. The DEDS B.T. and P.R. are also altered by approximately 45% and 40%, respectively, by blending of the SB resin in the PET-G resin.

II. Acoustical Properties

As stated previously, in addition to barrier properties, it is often desirable that a polymeric film not emit noise when crumpled. For example, in ostomy or incontinence applications, it is desirable that the ostomy or incontinence bag not emit noise. However, when crumpled, most polymeric films emit noise. In the case of multilayer barrier films, when polymers of high and low rigidities or modulus are combined, the multilayer film is significantly more noisy when crumpled than are films of the same thickness made only with the lowest modulus polymer.

TEST 6

Comparison of Noise and Modulus of Multilayered Films

A demonstration of the phenomenon that when polymers of high and low rigidities or modulus are combined in a multilayer film, the multilayer film is significantly more noisy when crumpled than are films of the same thickness made only with the lowest modulus polymer is shown in the following Comp Ex Q to W in Tables 12 and 13, wherein the composition of the films is described in Table 11.

Coextrude five layer symmetrical cast films of layer configuration A/B/C/B/A with LDPE or EVA skins and a rigid core layer of PET-G, ABS, amorphous PA or PC. These films have two tie layers, each representing 7.5% of the total film thickness. Also prepare monolayer cast films of the same composition as the skin layers and of comparable thickness. Table 11 lists the composition of these films. All resins are described in Table 5.

TABLE 11

| Comp. Ex. | Skin Layers A | Tie Layers B | Core Layer C | Core Layer Thickness µm | Total Thickness µm | Film Type |
|---|---|---|---|---|---|---|
| Q | LDPE-2 | — | — | — | 75 | monolayer |
| R | LDPE-2 | MAH-g-EVA-2 | PET-G | 7.5 | 78 | 5 layers |
| S | LDPE-2 | MAH-g-EVA-2 | ABS | 7.5 | 78 | 5 layers |
| T | LDPE-2 | MAH-g-EVA-2 | co-PA-1 | 6[1] | 76 | 5 layers |
| U | LDPE-2 | EMA | PC-3 | 8 | 95 | 5 layers |
| V | EVA-4 | — | — | — | 72 | monolayer |
| W | EVA-4 | MAH-g-EVA-2 | PET-G | 6.5 | 90 | 5 layers |

[1]in this film, the barrier layer is split into 5 alternating layers "barrier/tie". The sum of these barrier layers is reported There is a high difference in modulus (rigidity) between the skin and the core resins of these films as shown in Table 12.

Determination of the Storage Modulus (G') and Tangent Delta by Dynamic Mechanical Spectroscopy (D.M.S.)

Determine the G' of the films in Table 12 as follows:

Make dynamic mechanical measurements (i.e., G' and Tan Δ values) using one of two Rheometrics RDS-II instruments (S/N 024-12 and 024-40) running under Rheos 4.4.4 software for machine control and data collection. Test all samples using a dynamic temperature ramp profile, from −100° C. to approximately 150° C. at 2° C./min with a torsional frequency of 10 radians per second (rad/sec) and strain of 0.02%. Compression mold individual specimens prior to for testing. Specimen dimensions are approximately 12.7×3.2×57.2 mm (0.5×0.125×2.25 in).

TABLE 12

Storage modulus G' at 20° C.

| RESIN | G' (10E-5 Newton/cm²) |
|---|---|
| LDPE-2 | 1.57E + 09 |
| EVA-4 | 1.20E + 08 |
| PET-G | 7.3E + 09 |
| ABS | 1.03E + 10 |
| co-PA-1 | 1.08E + 10 |
| PC-3 | 8.64E + 09 |

Measure the noise of these films and report the results in Table 13.

Determine the noise of the films of Table 13 as follows:

Cut a 10×10 cm size sample in the film, with the machine (MD) and transverse direction (TD) parallel to the sides of the sample. Fix the specimen with double side adhesive tapes on two circular holders of a diameter of 32 mm and 90 mm distant of from each other. The film has the shape of a vertical cylinder (32 mm diameter) with one slit along its axis. The film MD is parallel to the axis of the cylinder. Make sure that folds from the cylindrical film sample are eliminated. The bottom circular holder is stationary while the upper holder is connected to an alternating drive mechanism.

Place a microphone 17 mm from the edge at half height of the film cylinder, at 90° from the slit. Connect the microphone to a CEL 393 noise analyzer having an octave frequency filter. Set the noise analyzer in "P" (peak) mode, range 2. Enclose the whole set-up, with the exception of the motor of the drive unit and the noise meter, in a sound insulated box (15 mm plywood/3 mm lead/8 cm rockwool from outside to inside). Internal dimensions of the box are 33 cm×33 cm×40 cm (length×width×height). After starting the motor, the film makes an alternative flexing motion with an angle of 65 degrees at the flexing frequency of 0.6 Hz. Record the noise made by the flexing motion of the film in the octave frequency bands from 16 Hz to 16 kHz in the decibel A scale [dBA]. Make 2 to 4 measurements and calculate an average for each frequency band. Conduct the test at ambient temperature (approximately 20° C.).

TABLE 13

Noise in dBA for different octave frequency bands

| Comp. EX | 63 Hz | 125 Hz | 250 Hz | 500 Hz | 1 kHz | 2 kHz | 4 kHz | 8 kHz | 16 kHz |
|---|---|---|---|---|---|---|---|---|---|
| Q | 36.2 | 46.2 | 58.5 | 60.8 | 62.5 | 65.1 | 68.4 | 61.9 | 48.9 |
| R | 49.3 | 54.4 | 66.6 | 77.3 | 76.1 | 78.1 | 75.7 | 71.0 | 65.4 |
| S | 47.7 | 54.5 | 65.6 | 72.3 | 75.2 | 78.6 | 76.6 | 71.5 | 63.3 |
| T | 45.2 | 54.1 | 65.0 | 70.9 | 72.1 | 77.4 | 75.1 | 71.8 | 64.2 |
| U | 50.9 | 58.0 | 69.6 | 73.8 | 75.6 | 77.3 | 75.3 | 71.4 | 63.6 |
| V | 37.6 | 38.1 | 41.6 | 44.3 | 43.0 | 47.0 | 42.8 | 35.5 | 25.7 |
| W | 38.8 | 50.3 | 57.5 | 62.9 | 69.2 | 74.1 | 73 | 68.2 | 54.6 |

Comp Ex R, S, T, U and W are significantly noisier than the films of Comp Ex Q and V which do not include the thin core layer of rigid resin. The higher noise of the films containing the rigid core layer is due to a lower "sound reduction index" or "SRI" of the film resulting from the incorporation of a layer of higher stiffness in the structure. Reducing the stiffness of a structure is a known method to increase its SRI. (See, for example, *Woods Practical Guide to Noise Control*, Fifth edition, March 1972, page 117. Published by Woods Acoustics, a division of Woods of Colchester Limited, UK). It may therefore be advantageous to find a method to reduce the noise of these coextruded structures containing a rigid layer. Rigid layer means that the G' modulus of this layer is $\geq 2\times10^4$ N/cm$^2$.

TEST 7

A) Determination of Noise for Multilayer Polymeric Films

Prepare six symmetrical 5-layer, co-extruded cast films A/B/C/B/A with the same rigid barrier layer (layer C), but with skin layers of different rigidities. These films have one ?PET-G co-polyester barrier layer and 2 tie layers representing 15 percent of the total thickness. Table 14 describes these films, and Table 22 reports the G' and Tan Δ values of the skin polymers.

TABLE 14

Films Description

| Comp. Ex. or Ex No. | Skin Layers A | Tie Layers B | Barrier Layer C | Total Thickness (μm) | Barrier Layer Thickness (μm) |
|---|---|---|---|---|---|
| X | LDPE-2/ADD-1 (96/4%) | MAH-g-EVA-2 | PET-G | 75 | 5.0 |
| Y | ITP-4/ADD-1 (96/4%) | MAH-g-EVA-2 | PET-G | 72 | 6.0 |
| Z | EMA/ADD-1 (96/4%) | MAH-g-EVA-2 | PET-G | 75 | 6.3 |
| AA | EMA/ITP-4/ADD-4 (48/48/4%) | MAH-g-EVA-2 ® 3860 | PET-G | 75 | 5.0 |
| 50 | PP/ADD-1 (96/4%) | MAH-g-EVA-2 | PET-G | 70 | 8.3 |
| 51 | PP/ITP-4/ADD-1 (48/48/4%) | MAH-g-EVA-2 | PET-G | 78 | 6.9 |

**Typical compositions of skin layers of Comp. Ex. Y is described in the patent Application WO 95/07816 entitled "Multilayer Barrier Film"

The noise of these films was measured and is reported in Table 15, wherein the noise is determined as described previously in Test 6.

TABLE 15

Film noise level in dBA versus Octave Frequency band

| Comp. Ex./-Ex No. | 63 Hz | 125 Hz | 250 Hz | 500 Hz | 1 kHz | 2 kHz | 4 kHz | 8 kHz | 16 kHz |
|---|---|---|---|---|---|---|---|---|---|
| X | 36.8 | 48.3 | 63.7 | 72.9 | 71 | 77.7 | 75.5 | 69.7 | 59.8 |
| Y | 38.5 | 48.4 | 56 | 59.6 | 62.4 | 72 | 74 | 67.6 | 57.9 |
| Z | 37.3 | 43.9 | 52.2 | 57 | 58.2 | 65.3 | 69.9 | 63.2 | 50.2 |
| AA | 37.9 | 45.5 | 54.8 | 60.5 | 60.6 | 69.8 | 75 | 67.2 | 49.2 |
| 50 | 38.1 | 42.6 | 51.3 | 56 | 57.4 | 65.4 | 67 | 56.6 | 40.7 |
| 51 | 38.5 | 45.6 | 54.6 | 57.5 | 60.9 | 66.6 | 68 | 61.1 | 39.3 |

Table 15 shows that, surprisingly, the quietest films are not the ones made with the skin resin composition of the lowest G' modulus. Ex 50 and 51 are the quietest films in almost the whole frequency spectrum although their skin resins have a G' modulus significantly higher than those of Comp Ex Y, Z and AA. The Tan Δ value of the skin resins of a film in the −5° C. to +15° C. temperature range plays a dominant role in reducing the noise of the coextruded structure. Ex 50 and 51 have the highest Tan Δ in this temperature range and are, therefore, quietest films. This clearly demonstrates why Ex 50 and 53 are significantly quieter than the films of Comp Ex X, Y, Z and AA.

Blending resins does not significantly alter the final result, as seen with the film of Ex 51 which has a noise intermediate between the films of Comp Ex Y and Ex 50 which are made with each of its skin components.

The quietest films are those that contain a polymeric resin having a Tan Δ value ≥0.25 at a temperature within the range between −5° C. and 15° C. or ≥0.32 at a temperature within the range between −12° C. and −5° C.

Surprisingly, when the co-extruded films contain some resins with good noise reduction characteristics (e.g., high Tan Δ value in the −12° C. to +15° C. temperature range) and relatively low G', thicker films are, contrary to expectations, quieter than thinner films at high frequencies. Test 7-C below supports this observation with Comp Ex AC and AD, as well as Ex 52 and 53.

At least one skin layer preferably comprises from 75 to 25 wt % of low crystallinity PP copolymer and from 25 to 75 wt % of a blend of low crystallinity homogeneous EAO copolymer and LLDPE or ULDPE. Also, the tie layers preferably each represent 3 to 15% of the total film thickness and are formed from an EVA or EMA copolymer having a co-monomer content ≧20 wt %.

B) Noise Determination for Multilayer Polymeric Films

These films are 5-layer, co-extruded cast films A/B/C/B/A with PET-G co-polyester barrier layer (layer C). The films of Comp Ex AB and AC have the same skin compositions, but different skin thickness; the films of Ex 52 and 53 have another skin composition and different skin thickness. All films have one barrier layer and two tie layers representing 15% of the total thickness. Table 16 describes the films. Table 22 reports the G' and Tan Δ values of the skin polymers.

TABLE 16

Films Description

| Comp. Ex/Ex No. | Skin Layers A | Tie Layers B | Barrier layer C | Total Thickness (μm) | Barrier Layer Thickness (μm) |
|---|---|---|---|---|---|
| AB | EVA-1/EVA-2/ADD-1 (72%/24%/4%) | MAH-g-EVA-2 | PET-G | 80 | 5.0 |
| AC | EVA-1/EVA-2/ADD-1 (72%/24%/4%) | MAH-g-EVA-2 | PET-G | 95 | 4.8 |
| 52 | PCP-2/ADD-1 (92%/8%) | MAH-g-EVA-2 | PET-G | 79 | 9.4 |
| 53 | PCP-2/ADD-1 (92%/8%) | MAH-g-EVA-2 | PET-G | 90 | 10.0 |

The noise of these films is reported in Table 17, wherein the noise is determined as described previously in Test 6.

TABLE 17

Film noise level in dBA versus Octave Frequency band

| Comp. Ex/Ex No | 63 Hz | 125 Hz | 250 Hz | 500 Hz | 1 kHz | 2 kHz | 4 kHz | 8 kHz | 16 kHz |
|---|---|---|---|---|---|---|---|---|---|
| AB | 37.2 | 46 | 53.3 | 58.9 | 61.7 | 70.6 | 73.5 | 64 | 55.1 |
| AC | 37.5 | 48.8 | 59.7 | 63.6 | 65.1 | 74.2 | 75.6 | 69.1 | 58.1 |
| 52 | 37.6 | 41.1 | 49.7 | 55.6 | 58.6 | 67.6 | 66.9 | 56.6 | 37.2 |
| 53 | 37.9 | 44.5 | 53.8 | 57.1 | 60.1 | 66 | 64.9 | 55.1 | 31 |

The film of Comp Ex AC is noisier than the film of Comp Ex AB at all frequency ranges, while the film of Ex 53 is noisier than the film of Ex 52 only up to 1 kHz, but is quieter from 2 to 16 kHz (i.e., the most annoying frequencies for the human ear).

C) Determination of Noise for Multilayer Polymeric Films

Prepare eight symmetrical 5-layer, co-extruded cast films A/B/C/B/A with the same rigid barrier layer, but with skin layers of different G' and Tan Δ values. These films have one PET-G co-polyester barrier layer and two tie layers representing 15% of the total thickness. Table 18 describes these films. Table 22 provides the G' and Tan Δ values of the skin polymers can be found in Table 22, and in FIGS. 1, 2, 4, 7, 8, 9 and 10. Table 18 also reports Comp Ex X with LDPE skin layers as a control film.

TABLE 18

Film Descriptions

| Comp. Ex/Ex No | Skin Layers A | Tie Layers B | Barrier Layer C | Total Thickness (μm) | Barrier Layer Thickness (μm) |
|---|---|---|---|---|---|
| X | LDPE-2 | MAH-g-EVA-2 | PET-G | 75 | 5.0 |
| AD | PP-EPDM/ADD-1 (98/2%) | MAH-g-EVA-2 | PET-G | 75 | 6.0 |
| 54 | PP/PP-EPDM/ADD-1 (72/24/4%) | MAH-g-EVA-2 | PET-G | 80 | 7.5 |
| 55 | PCP-3/ADD-1 (92/8%) | MAH-g-EVA-2 | PET-G | 85 | 6.0 |
| 56 | PCP-2/ADD-1 (92/8%) | MAH-g-EVA-2 | PET-G | 79 | 9.4 |
| 57 | PP/PCP-1/ADD-1 (72/24/4%) | MAH-g-EVA-2 | PET-G | 77 | 10 |
| 58 | PP/PCP-2/ADD-1 (72/24/4%) | EMA | PET-G | 74 | 8.5 |
| 59 | PCP-1/ITP-4/ADD-1 (46/46/8%) | EVA-3 | PET-G | 76 | 9.2 |

Table 19 summarizes noise measurements of these films, with noise being determined as in Test 6.

TABLE 19

Film noise level in dBA versus Octave Frequency band

| Comp. Ex/Ex No. | 63 Hz | 125 Hz | 250 Hz | 500 Hz | 1 kHz | 2 kHz | 4 kHz | 8 kHz | 16 kHz |
|---|---|---|---|---|---|---|---|---|---|
| X | 36.8 | 48.3 | 63.7 | 72.9 | 71 | 77.7 | 75.5 | 69.7 | 59.8 |
| AD | 43.7 | 50.7 | 55.9 | 57.9 | 57.8 | 64.7 | 66.7 | 64.1 | 52 |
| 54 | 36.9 | 43.5 | 52.4 | 55.3 | 59.2 | 66.9 | 65.3 | 58.3 | 38.8 |
| 55 | 37.2 | 43.8 | 49.2 | 52.2 | 53.9 | 61.2 | 60.9 | 48.6 | 28.4 |
| 56 | 36.3 | 43.6 | 51.2 | 55.7 | 57.9 | 67.2 | 66.9 | 57.1 | 41.6 |
| 57 | 37.9 | 46 | 55.7 | 59.6 | 61 | 63.8 | 64.3 | 54 | 37.7 |
| 58 | 38 | 41.5 | 53.2 | 59.4 | 60.6 | 67 | 68.7 | 58.5 | 49.6 |
| 59 | 36.4 | 46.4 | 54.1 | 57.3 | 58.8 | 65 | 65.8 | 62.4 | 49.3 |

The data of Table 19 clearly shows that the film of Comp Ex AD is quieter than the film of Comp Ex X mainly because of the G' value of its skin resin which is approximately 30–40 times lower. On the other hand, the films of Ex 54 to 59 are essentially quieter than the films of Comp Ex X and AD, mainly in the frequency range of 1 kHz and above because their composition contains a significant proportion of a polymer having a Tan Δ value ≧0.25 at a temperature within the range between −5° C. and 15° C. or ≧0.32 at a temperature within the range between −12° C. and −5° C., while their G' value is in the same range as LDPE (See Table 22). Low crystallinity PP homo- or copolymer resins, as used in Ex 54 to 59, are particularly efficient noise dampening polymers. Low crystallinity PP, as used herein, means that the heat of fusion (Hf) of the resin is significantly lower than that of regular isotactic PP, e.g. ≦50 J/g.

D) Noise Determination for Multilayer Polymeric Films

Prepare four symmetrical 5-layer, co-extruded cast films A/B/C/B/A with the same rigid barrier layer, but with skin layers of different G' and Tan Δ values. These films have an amorphous co-polyamide barrier layer and two tie layers representing 15% of the total thickness. The G' and Tan Δ values of the skin polymers can be found in Table 22.

TABLE 20

Film Descriptions

| Comp. Ex/Ex. No. | Skin Layers A | Tie Layers B | Barrier Layer C | Total Thickness (μm) | Barrier Layer Thickness (μm) |
|---|---|---|---|---|---|
| AE | LDPE-2 | MAH-g-EVA-2 | co-PA-1 | 86 | 9.6(**) |
| AF | EVA-1/ADD-1 (95%/5%) | MAH-g-EVA-2 | co-PA-1 | 75 | 10.0 |
| 60 | PCP-2/ITP-4/ADD-1 (46%/46%/8%) | MAH-g-EVA-2 | co-PA-1 | 75 | 7.5 |
| 61 | PCP-2/ITP-4/ADD-1 (46%/46%/8%) | MAH-g-EVA-2 | co-PA-1 | 75 | 9.0 |

**: in this film, the barrier layer is split into 5 alternating layers "barrier/tie". The sum of these barrier layers is reported Table 21 summarizes noise measurements of these films, with noise being determined as in Test 6.

TABLE 21

Film noise level in dBA versus Octave Frequency band

| Comp. Ex/Ex. No. | 63 Hz | 125 Hz | 250 Hz | 500 Hz | 1 kHz | 2 kHz | 4 kHz | 8 kHz | 16 kHz |
|---|---|---|---|---|---|---|---|---|---|
| AE | 51.8 | 56.3 | 66.4 | 76.5 | 77.3 | 78.6 | 75.4 | 72.6 | 66.2 |
| AF | 42.5 | 54.1 | 66.7 | 70.7 | 74.6 | 76.6 | 76.7 | 75.2 | 65.8 |
| 60 | 36.0 | 39.5 | 50.5 | 52.7 | 55.8 | 64.4 | 61.8 | 56.1 | 42.3 |

TABLE 21-continued

Film noise level in dBA versus Octave Frequency band

| Comp. Ex/Ex. No. | 63 Hz | 125 Hz | 250 Hz | 500 Hz | 1 kHz | 2 kHz | 4 kHz | 8 kHz | 16 kHz |
|---|---|---|---|---|---|---|---|---|---|
| 61 | 38.9 | 44.6 | 58.0 | 60.0 | 63.7 | 73.3 | 70.6 | 68.3 | 54.9 |

Ex 60 and 61 are significantly quieter than Comp Ex AE and AF. This clearly shows that the significant noise reduction of multilayer films obtained by the use of polymeric resin having a Tan Δ value ≧0.25 at a temperature within the range between −5° C. and 15° C. or ≧0.32 at a temperature within the range between −12° C. and 5° C. in the film composition is not restricted to films containing a layer of PET-G, but is also achieved by combining resins of high and low modulus in a same film structure.

Measure the noise of all Ex at room temperature (approx. 20° C.). It is anticipated that if the noise is measured at a different temperature, the same noise reduction effect shall be obtained with polymers having a Tan Δ value ≧0.25 in a temperature range shifted by the same temperature difference.

Table 22 gives the Maximum Tan Δ values, G' values, and Tan Δ values at selected temperatures for resins used in Tests 6–8, with the determination of the G' and Tan Δ values as in Test 6. Skilled artisans recognize that G' and Tan Δ values are readily portrayed as curves rather than discrete values. The values shown in Table 22 merely illustrate points on the curve and do not limit this invention to those points. The invention includes all points on the curve that meet the criteria specified herein.

TABLE 22

Maximum Tan Δ, G' and Tan Δ Values at selected Temperatures

| Resin | Max Tan Δ ° C. | Max Tan Δ value | Tan Δ value at selected temperatures | | | | | | |
|---|---|---|---|---|---|---|---|---|---|
| | | | −20° C. | −10° C. | 0° C. | 10° C. | 20° C. | 30° C. | 40° C. |
| PP | 2.2 | 0.46 | 0.03 | 0.068 | 0.43 | 0.313 | 0.16 | 0.125 | 0.13 |
| PCP-1 | 1.6 | 0.41 | 0.028 | 0.074 | 0.395 | 0.291 | 0.167 | 0.12 | 0.115 |
| PCP-2 | 1.5 | 0.59 | 0.033 | 0.099 | 0.575 | 0.366 | 0.186 | 0.134 | 0.137 |
| PCP-3 | 0.2 | 0.64 | 0.037 | 0.14 | 0.644 | 0.349 | 0.178 | 0.135 | 0.137 |
| EVA-4 | −19 | 0.28 | 0.27 | 0.249 | 0.21 | 0.154 | 0.08 | 0.053 | 0.06 |
| ITP-4 | −15 to 0[1] | 0.19 | 0.19 | 0.19 | 0.19 | 0.168 | 0.12 | 0.072 | 0.05 |
| LDPE-2 | 63 | 0.23 | 0.08 | 0.092 | 0.01 | 0.11 | 0.13 | 0.14 | 0.17 |
| EMA | −21.6 | 0.317 | 0.312 | 0.24 | 0.189 | 0.123 | 0.066 | 0.049 | 0.053 |
| PP-EPDM | −21 | 0.305 | 0.3 | 0.218 | 0.165 | 0.122 | 0.077 | 0.066 | 0.078 |
| EVA-1 | −15 | 0.20 | 0.197 | 0.20 | 0.192 | 0.188 | 0.158 | 0.10 | 0.06 |
| EVA-2 | −18.5 | 0.23 | 0.23 | 0.217 | 0.21 | 0.189 | 0.125 | 0.071 | 0.06 |

Storage modulus G' at selected temperatures (G' in $10E^{-5}$ N/cm²)

| Resin | −20° C. | −10° C. | 0° C. | 10° C. | 20° C. | 30° C. | 40° C. |
|---|---|---|---|---|---|---|---|
| PP | 1.10E+10 | 1.01E+10 | 4.20E+09 | 8.18E+08 | 4.70E+08 | 3.60E+08 | 2.40E+08 |
| PCP-1 | 1.12E+10 | 9.91E+09 | 3.24E+09 | 8.91E+08 | 5.34E+08 | 3.97E+08 | 2.97E+08 |
| PCP-2 | 1.05E+10 | 8.94E+09 | 1.89E+09 | 4.01E+08 | 2.41E+08 | 1.74E+08 | 1.27E+08 |
| PCP-3 | 1.08E+10 | 8.50E+09 | 1.41E+09 | 3.27E+08 | 2.05E+08 | 1.58E+08 | 1.23E+08 |

TABLE 22-continued

Maximum Tan Δ, G' and Tan Δ Values at selected Temperatures

| | | | | | | | |
|---|---|---|---|---|---|---|---|
| EVA-4 | 1.20E+09 | 4.82E+08 | 2.50E+08 | 1.56E+08 | 1.20E+08 | 9.25E+07 | 5.70E+07 |
| ITP-4 | 1.45E+09 | 8.87E+08 | 5.71E+08 | 3.99E+08 | 2.92E+08 | 2.33E+08 | 1.72E+08 |
| LDPE-2 | 4.68E+09 | 3.53E+09 | 2.70E+09 | 2.10E+09 | 1.57E+09 | 1.18E+09 | 8.11E+08 |
| EMA | 8.60E+08 | 3.66E+08 | 2.17E+08 | 1.40E+08 | 1.08E+08 | 9.00E+07 | 6.45E+07 |
| PP-EPDM | 2.91E+08 | 1.32E+08 | 8.22E+07 | 5.38E+07 | 4.11E+07 | 3.46E+07 | 2.55E+07 |
| EVA-1 | 1.98E+09 | 1.90E+09 | 5.80E+08 | 3.57E+08 | 2.47E+08 | 1.85E+08 | 1.50E+08 |
| EVA-2 | 1.70E+09 | 8.18E+08 | 4.54E+08 | 2.81E+08 | 1.97E+08 | 1.47E+08 | 9.68E+07 |

[1]broad peak

III. Heat Seal Strength Properties

As described previously, it may be desirable for the end use application to seal some of the multi-layer films, for example, to produce bags. The seal strength of some skin polymer compositions may be too low when the film is sealed to itself or to other polymers. A higher seal strength may be obtained by adding a sealant layer to the outermost layer of the film, or by blending into the outermost layer a polymer that improves the seal strength.

TEST 9

Determination of Heat Seal Strength of Mulilayered Polymeric Films

Table 23 (5-layer, co-extruded films A/B/C/B/A with two tie layers, B, representing 15% of the total thickness) demonstrates that a higher seal strength may be obtained by blending into the composition some other polymer that improves the seal strength. In this regard, blends comprising a low crystallinity EAO copolymer and LLDPE or ULDPE are advantageous and preferred.

Determine the heat seal strength of the films in Table 23 as follows:

Heat seal two pieces of film together on a laboratory heat sealer as detailed below.

Use 20 N/cm$^2$ sealing pressure, and 1.5 sec sealing time. Heat the upper sealing jaw at 180° C. (film/film) or 225° C. (film/LDPE), while the lower jaw is at 50° C. Interpose a 13 μm thick polyester film between the film and the sealing bars to prevent sticking. The seal is parallel to the film TD. Cut 25.4 mm wide heat sealed specimens and put them in the clamps of a tensile tester having 50 mm distance between the, two clamps. Pull the two sides of the seal apart at a speed of 508 mm/min in the film's MD. Record the maximum force required to break the specimen as the seal strength. For the seal strength film/film, seal the film on itself. For the seal strength film/LDPE, seal the film on a LDPE based film (70 μm thickness, a blend of 75 wt % of LDPE melt index (M.I.)=1.75 g/10 min, density (d)=0.924 g/cm$^3$ and 25 wt % of LLDPE (octene copolymer) M.I.=2.3 g/10 min, d=0.917 g/cm$^3$). Place the LDPE film on the lower jaw of the heat sealer to prepare the seal.

TABLE 23

Composition and Seal Strength of Films

| Ex No. | Skin Layers A | Tie Layers B | Barrier Layer C | Total Thickness (μm) | Barrier Layer Thickness (μm) | Seal Strength Film/Film (N/25 mm) | Seal Strength Film/LDPE (N/25 mm) |
|---|---|---|---|---|---|---|---|
| 50 | PCP-1/ADD-1 (96/4%) | MAH-g-EVA-2 | PET-G | 70 | 8.3 | 14.5 | 1.1 |
| 57 | PCP-1/PCP-2/ADD-1 (72/24/4%) | MAH-g-EVA-2 | PET-G | 77 | 10 | 10.4 | 1.5 |
| 51 | PCP-1/ITP-4/ADD-1 (48/48/4%) | MAH-g-EVA-2 | PET-G | 78 | 6.9 | 17.0 | 13.9 |
| 62 | PCP-1/ITP-4/ADD-1 (46/46/8%) | EVA-3 | PET-G | 80 | 7.0 | 22.3 | 18.7 |
| 63 | PCP-2/ITP-4/ADD-1 (69/23/8%) | EVA-3 | PET-G | 75 | 6.0 | 18.0 | 17.2 |
| 64 | PCP-2/ITP-4/ITP-1/ADD-1/ADD-4/ADD-3/ADD-2 (46/21.3/21.2/6/3.5/2%) | EVA-3 | PET-G | 80 | 6.0 | 21.4 | not determined |
| 65 | PCP-2/ITP-4/ULDPE-3/ADD-1/ADD-4/ADD-3/ADD-2 (46/21.3/21.2/6/3.5/2%) | EVA-3 | PET-G | 75 | 6.0 | 20.2 | not determined |

TABLE 23-continued

Composition and Seal Strength of Films

| Ex No. | Skin Layers A | Tie Layers B | Barrier Layer C | Total Thickness (μm) | Barrier Layer Thickness (μm) | Seal Strength Film/Film (N/25 mm) | Seal Strength Film/ LDPE (N/25 mm) |
|---|---|---|---|---|---|---|---|
| 66 | PCP-2/ITP-3/ULDPE-3/ADD-1/ADD-4/ADD-3/ADD-2 (46/10.6/31.9/6/3.5/2%) | EVA-3 | PET-G | 81 | 7.0 | 19.6 | not determined |
| 67 | PCP-2/ITP-2/ULDPE-1/ADD-1/ADD-4/ADD-3/ADD-2 4420 (46/19.1/23.4/6/3.5/2%) | EVA-3 | PET-G | 75 | 7.0 | 21.1 | not determined |
| 68 | PCP-2/ITP-3/ULDPE-2/ADD-1/ADD-4/ADD-3/ADD-2 (46/17/25.5/6/3.5/2%) | EVA-3 | PET-G | 74 | 8.0 | 20.4 | not determined |

Comparing Ex 51 and 62 to 68 with Ex 50 and 57 shows that blending some low crystallinity homogeneous EAO copolymer or some ULDPE and low crystallinity homogeneous EAO copolymer in the low crystallinity PP improves the seal strength of the films.

Ex 50 and 57 have acceptable heat seal strength on themselves, but very low seal strength onto LDPE, while the films of Ex 51, 62 and 63 have stronger seal strength on themselves as well as on LDPE. These compositions are also advantageous when the film must be sealed on a polyolefin article like LDPE.

III. Tie Resin Selection

Alternative resins to EVA copolymers can be used as tie resins between a PET-G-based layer and a polyolefin-based layer in a coextruded film structure. Table 24 (5-layer, co-extruded films, A/B/C/B/A with two tie layers, B, representing 15% of the total thickness) data demonstrate that adequate seal strength can be obtained by using EMA copolymers instead of EVA.

Other tie resins useful in the present invention can be selected from MAH- or glycidyl methacrylate grafted EVA, EMA or EBA, ethylene-acrylic ester-glycidyl methacrylate terpolymers, ethylene-glycidyl methacrylate copolymers, ethylene-acrylic ester-maleic anhydride terpolymers, SB copolymers, EVACO terpolymers, styreneisoprene copolymers and blends thereof.

Ex 70–74

Prepare four five-layer symmetrical coextruded films (Ex 70–73) and one seven-layer symmetrical coextruded film (Ex 74). The five layer films have an A/B/C/B/A structure and the seven layer film has an A/B/C/D/C/B/A structure. Table 25 provides layer thickness and composition for Ex 70–73. The barrier core layer for Ex 70 constitutes PET-G. The barrier core layer for Ex 71–74 constitutes a blend of PET-G and APE-1. For Ex 74, the respective layer compositions and thicknesses are: A=93 wt % ITP-1 and 7 wt % ADD-1, 8 μm per layer; B=100 wt % PCP-2, 26.5 μm per layer; C=100 wt % EVA-3, 5.6 μm per layer; and D=70 wt % PET-G and 30 wt % APE-1 , 4.8 μm.

TABLE 24

Composition and Seal Strength of Films

| Ex. No. | Skin Layers A | Tie Layers B | Barrier Layer C | Total Thickness (μm) | Barrier Layer Thickness (μm) | Seal Strength Film/Film (N/25 mm, MD) |
|---|---|---|---|---|---|---|
| 69 | PCP-2/ITP-4/ADD-1 (46/46/8%) | EMA | PET-G | 75 | 7.5 | 23.7 |

*Trademark of The Dow Chemical Company

TABLE 25

| Ex No. | Skin Layer A | Tie Layer B | Barrier Layer C |
|---|---|---|---|
| 70 | PCP-2/ITP-2/ULDPE-1/ADD-1 (46/19.2/23.3/11.5%) 41.3 μm | EVA-3, 7.5 μm | PET-G, 10.4 μm |
| 71 | PCP-2/ITP-2/ULDPE-1/ADD-1 (46/19.2/23.3/11.5%) 39.6 μm | EVA-3, 7.5 μm | PET-G/APE-1 (70/30) 9.9 μm |
| 72 | PCP-2/ITP-2/ULDPE-1/ADD-1 (46/21.2/25.8/7%) 38.9 μm | MAH-g-EVA-2/ADD-1 (98/2%), 7.5 μm | PET-G/APE-1 (50/50) 4.5 μm |

TABLE 25-continued

| Ex No. | Skin Layer A | Tie Layer B | Barrier Layer C |
|---|---|---|---|
| 73 | PCP-2/ITP-2/ULDPE-1/ADD-1 (46/21.2/25.8/7%) 40.8 μm | EVA-3, 7.5 μm | PET-G/APE-1 (50/50) 6.7 μm |

Subject the multilayer films of Ex 70–74 to noise testing as described above, but use a different noise meter. The meter is a NC10 audio acoustic analyzer (Neutrik Cortex Instruments) that analyzes noise by ⅓ octave frequency bands rather than full octave bands as with the CEL noise analyzer. This effectively triples the number of frequency band samplings. Begin testing at a frequency of 1 Hz, with a 30 sec measurement time, fast function, equipment setting EXP EC, and minimum range using a microphone placed 15 mm from the film rather than 17 mm as in previous testing. Summarize the test results in Table 26.

TABLE 26

| | Noise Level in dB(A) by Ex No. | | | | |
|---|---|---|---|---|---|
| Freq (Hz) | 70 | 71 | 72 | 73 | 74 |
| 63 | 23.7 | 24.0 | 25.1 | 25.2 | 30.4 |
| 80 | 29.2 | 28.5 | 20.2 | 21.0 | 22.8 |
| 100 | 22.5 | 22.7 | 22.5 | 24.5 | 25.2 |
| 125 | 26.7 | 26.9 | 27.8 | 29.8 | 28.6 |
| 160 | 32.7 | 32.7 | 33.7 | 35.7 | 33.9 |
| 200 | 39.0 | 38.6 | 38.8 | 41.1 | 36.7 |
| 250 | 43.0 | 42.0 | 42.7 | 43.8 | 38.2 |
| 315 | 45.3 | 43.4 | 45.2 | 45.2 | 38.6 |
| 400 | 46.6 | 46.2 | 45.9 | 45.8 | 40.5 |
| 500 | 46.3 | 46.2 | 45.8 | 46.0 | 41.2 |
| 630 | 45.0 | 44.3 | 44.7 | 45.6 | 40.7 |
| 800 | 44.3 | 43.8 | 44.2 | 45.3 | 40.2 |
| 1000 | 44.7 | 4.37 | 44.2 | 44.9 | 39.2 |
| 1250 | 44.9 | 44.1 | 44.1 | 45.9 | 39.2 |
| 1600 | 45.9 | 44.9 | 45.6 | 47.7 | 40.7 |
| 2000 | 51.7 | 50.4 | 52.1 | 54.1 | 46.1 |
| 2500 | 50.0 | 50.1 | 50.3 | 52.4 | 47.1 |
| 3150 | 43.6 | 45.1 | 45.1 | 45.8 | 42.7 |
| 4000 | 40.2 | 42.1 | 43.0 | 42.7 | 39.9 |
| 5000 | 40.2 | 42.1 | 43.0 | 43.0 | 36.3 |
| 6300 | 38.3 | 39.5 | 39.8 | 39.2 | 31.7 |
| 8000 | 32.9 | 37.4 | 34.7 | 36.8 | 30.0 |
| 10000 | 27.6 | 32.2 | 27.9 | 26.8 | 26.0 |
| 12500 | 21.9 | 27.3 | 20.8 | 21.2 | 18.2 |
| 16000 | 16.1 | 21.3 | 8.9 | 13.5 | 7.6 |

The data in Table 26 show that the multilayer films of Ex 70–74 have potential utility as quiet films based upon the noise ratings that predominantly fall below 50 dB(A) over the frequency range shown in Table 26.

Subject the films of Ex 70–73 to barrier testing and summarize the results in Table 27.

TABLE 27

| Chemical | Test* | Units | Ex 70 | Ex 71 | Ex 72 | Ex 73 |
|---|---|---|---|---|---|---|
| $H_2S$ | Permeability | $Cm^3/m^2$-day | 23.6 | 8.8 | 5.9 | 4.9 |
| $H_2S$ | B.T. | Sec | 455 | 575 | 695 | 1010 |
| DEDS | B.T. | Min | 194 | 270 | 151 | 179 |
| 3-methyl indole | B.T. | Hrs | 100 | 45 | 110 | 120 |

*Perm = permeability; B.T. = breakthrough time

The data in Table 27 show that the multilayer films of Ex 70–73 have barrier properties similar to or better than the film of Comp Ex C. Films 71–74 containing the B-100 co-polyester have significantly lower permeability to H2S than film 70.

Determine heat seal properties as in Test 9 for Ex 72 and 73, and, for Ex 70–73, modulus as in test 5 and elongation at break (Elong @ Break) and break stress in accord with test 9 (ASTM F88)in both the machine direction (MD) and transverse direction (TD). Ex 72 has a film/film seal strength of 22.3 N/25 mm at a sealing temperature of 182° C. and 23.6 N/25 mm at 193° C. Ex 73 has a film/film seal strength of 20.9 N/25 mm at a sealing temperature of 193° C. and film/LDPE seal strengths of 9.8, 16.9 and 18.7 N/25 mm at respective sealing temperatures of 138° C., 149° C. and 171° C. Summarize remaining physical property test results in Table 28 and provide the test data for multilayer films of Comp Ex A and Comp Ex D, the latter two representing films currently used in fabricating ostomy bags.

TABLE 28

| Test | Ex 70 | Ex 71 | Ex 72 | Ex 73 | Comp Ex A | Comp Ex D |
|---|---|---|---|---|---|---|
| Elong @ Break MD(%) | 328 | 330 | 293 | 443 | 450 | 465 |
| Elong @ Break TD(%) | 350 | 369 | 449 | 485 | 483 | 533 |
| Break Stress MD(MPa) | 19.5 | 19.6 | 18.8 | 21.7 | 25.1 | 18.0 |
| Break Stress TD(MPa) | 16.2 | 17.3 | 15.4 | 17.5 | 17.2 | 14.3 |
| 1% Secant Modulus TD(MPa) | 250 | 292 | 223 | 149 | 170 | 120 |
| 1% Secant Modulus MD (MPa) | 210 | 285 | 218 | 148 | 160 | 120 |
| Seal strength film/film MD(N/25 mm) | n.d. | n.d. | 22.3 | n.d. | 27.7 | 21.3 | n.d. = not determined

Table 28 shows that the films of Ex 70–72 have satisfactory film physical properties similar to those of Comp Ex A and D. Other film structures that fall within the scope of the present invention should provide similar results.

Ex 75 and Comp Ex AG

Prepare a two-layer co-extruded film wherein one layer contains PET-G and has a thickness of 12 μm and the other layer contains EVA-3 and as additives, 0.2 wt % erucamide, 0.2 wt % stearamide and 0.1 wt % silicon dioxide, all percentages based on layer weight, and having a thickness of 38 μm.

Use a two layer film laminate similar to a commercial TDDS backing layer film as Comp Ex AG. The laminate has an overall thickness of 50.8 μm, including a 12 μm thick layer of a polyester such as polyethylene terephthalate and the balance being a layer of an ethylene-vinyl acetate copolymer.

The laminate of Comp Ex AG has a 2% modulus in both MD and TD that is significantly higher than that of the film of Ex 75, perhaps as much as double that of Ex 75, if not more. At the same time, the laminate of Comp Ex AG has an Elongation at Break in both MD and TD that is substantially lower than that of the film of Ex 75, often less than one-half that of the Ex 75 film.

The film of Ex 75 should provide a barrier to chemicals contained in a TDDS device or patch equivalent to that of the laminate of Comp Ex AG or nearly so. At the same time, the film of Ex 75 should provide greater comfort to one who wears the patch as a result of the lower modulus. The lower modulus of Ex 75 also promotes improved, relative to Comp Ex 75, patch conformability to a wearer's skin. The coextruded film of Ex 75 should also have a lower tendency to delaminate than the Comp Ex AG laminate.

What is claimed is:

1. A multilayer film structure that comprises at least one quiet film layer having noise dampening properties, said quiet layer comprising at least one polymer resin or polymer resin composition having a Tangent Delta value of at least 0.25 at a temperature within the range between −5° C. and 15° C. or at least 0.32 at a temperature within the range of from −12° C. to −5° C., and at least one second layer having a storage modulus G' equal to or greater than $2 \times 10^4$ N/cm$^2$.

2. The multilayer film of claim 1, wherein the second layer comprises a polymer selected from an amorphous thermoplastic polyester or a blend of essentially amorphous thermoplastic polyesters, a glycol-modified polyester, polyethylene terephthalate or polybutylene terephthalate, ethylene-vinyl alcohol polymers, polycarbonates, polyvinyl alcohols, styrene-acrylonitrile copolymers, acrylonitrile-butadiene-styrene terpolymers, poly(methyl methacrylate), styrene-butadiene copolymers, polyacrylonitrile, a polyamide or co-polyamide selected from PA-6, PA-6,6, PA-11, and PA-12, amorphous polyamides, MXD6 polyamide, polyvinylidene chloride, vinlylidene chloride-vinyl chloride copolymers, vinylidene chloride-methylacrylate copolymers, PHAE, polyurethanes, epoxies, PEN, syndiotactic polystyrene, and polystyrene.

3. An article of manufacture fabricated from the film of claim 1, the article being selected from ostomy bags, transdermal delivery systems, cosmetic patches, incontinence bags, medical collection bags or parenteral solution bags, odorous food packaging or protective clothing.

4. A multilayer film structure that comprises at least one quiet film layer having noise dampening properties, said quiet layer comprising at least one polymer resin or polymer resin composition selected from low crystallinity polypropylene, a blend of an amorphous poly (alpha-olefin) and a random propylene homopolymer or copolymer, ethylene-styrene interpolymer or polynorbornene in an amount of 25 weight percent or more and having a Tangent Delta value of at least 0.25 at a temperature within the range between −5° C. and 15° C. or at least 0.32 at a temperature within the range of from −12° C. to −5° C., and at least one second layer having a storage modulus G' equal to or greater than $2 \times 10^4$ N/cm$^2$.

5. The multilayer film of claim 4 wherein the amount is 30 weight percent or more.

6. The multilayer film of claim 4, wherein the second layer comprises a polymer selected from an amorphous thermoplastic polyester or a blend of essentially amorphous thermoplastic polyesters, a glycol-modified polyester, polyethylene terephthalate or polybutylene terephthalate, ethylene-vinyl alcohol polymers, polycarbonates, polyvinyl alcohols, styrene-acrylonitrile copolymers, acrylonitrile-butadiene-styrene terpolymers, poly(methyl methacrylate), styrene-butadiene copolymers, polyacrylonitrile, a polyamide or co-polyamide selected from PA-6, PA-6,6, PA-11, and PA-12, amorphous polyamides, MXD6 polyamide, polyvinylidene chloride, vinlylidene chloride-vinyl chloride copolymers, vinylidene chloride-methylacrylate copolymers, PHAE, polyurethanes, epoxies, PEN, syndiotactic polystyrene, and polystyrene.

7. An article of manufacture fabricated from the film of claim 4, the article being selected from ostomy bags, transdermal delivery systems, cosmetic patches, incontinence bags, medical collection bags or parenteral solution bags, odorous food packaging or protective clothing.

\* \* \* \* \*